(12) United States Patent
Simon

(10) Patent No.: US 6,820,037 B2
(45) Date of Patent: Nov. 16, 2004

(54) VIRTUAL NEURO-PSYCHOLOGICAL TESTING PROTOCOL

(75) Inventor: Ely Simon, Hashmonaim (IL)

(73) Assignee: Neurotrax Corporation, Bayside, NY (US)

( * ) Notice: Subject to any disclaimer, the term of this patent is extended or adjusted under 35 U.S.C. 154(b) by 70 days.

(21) Appl. No.: 10/362,085

(22) PCT Filed: Sep. 6, 2001

(86) PCT No.: PCT/IL01/00842

§ 371 (c)(1), (2), (4) Date: Feb. 19, 2003

(87) PCT Pub. No.: WO02/19889

PCT Pub. Date: Mar. 14, 2002

(65) Prior Publication Data

US 2003/0167149 A1 Sep. 4, 2003

(30) Foreign Application Priority Data

Sep. 7, 2000 (IL) .............................................. 138322

(51) Int. Cl.$^7$ .............................................. G06F 11/30
(52) U.S. Cl. ...................................... 702/182; 702/183
(58) Field of Search ......................... 434/236; 600/300; 702/182, 183, 188; 705/1, 2, 3

(56) References Cited

U.S. PATENT DOCUMENTS

| | | | | | |
|---|---|---|---|---|---|
| 5,660,176 A | * | 8/1997 | Iliff | ............................. | 600/300 |
| 5,711,297 A | * | 1/1998 | Iliff | ............................. | 600/300 |
| 5,724,968 A | * | 3/1998 | Iliff | ............................. | 600/300 |
| 5,868,669 A | * | 2/1999 | Iliff | ............................. | 600/300 |
| 5,910,107 A | * | 6/1999 | Iliff | ............................. | 600/300 |
| 5,961,332 A | * | 10/1999 | Joao | ............................. | 434/236 |
| 6,022,315 A | * | 2/2000 | Iliff | ............................. | 600/300 |
| 6,053,739 A | | 4/2000 | Stewart et al. | | |
| 6,071,236 A | * | 6/2000 | Iliff | ............................. | 600/300 |
| 6,113,540 A | * | 9/2000 | Iliff | ............................. | 600/300 |
| 6,120,440 A | * | 9/2000 | Goknar | ............................. | 600/300 |
| 6,206,829 B1 | * | 3/2001 | Iliff | ............................. | 600/300 |
| 6,334,778 B1 | * | 1/2002 | Brown | ............................. | 434/258 |
| 6,482,156 B2 | * | 11/2002 | Iliff | ............................. | 600/300 |

\* cited by examiner

*Primary Examiner*—John Barlow
*Assistant Examiner*—Douglas N Washburn
(74) *Attorney, Agent, or Firm*—Baker Botts LLP

(57) ABSTRACT

The present invention software driven protocol for managing a virtual clinical neuro-psychological testing program delivers, to individual or small groups of certified Neuropsychology professionals, an interface protocol for clinically monitoring and managing the neuro-psychological needs of very large numbers of individual patients. The preferred approach to such monitoring and testing, is within the scope of normal and routine activities. These patients are most often in need of regular testing, screening, and monitoring and, only occasionally, of referral or intervention. The protocol provides a majority of patients, with regular testing, screening, and monitoring services on a "virtual-out-patient" basis by interactively delivering individually configured batteries of tests to each patient; via the Internet. These tests include normal activity observation and monitoring. The delivery and respectively corresponding acceptance of the testing batteries is a substantially automatically scheduled feature of the protocol.

57 Claims, 17 Drawing Sheets

VIRTUAL NEURO-PSYCHOLOGICAL TESTING PROTOCOL

CROSS-REFERENCE TO RELATED APPLICATIONS

This application is a national stage application of PCT Application No. PCT/IL01/00842 which was filed on Sep. 6, 2001 and published in English on Mar. 14, 2002 as International Publication No. WO 02/19889 (the "International Application"). This application claims priority from the International Application pursuant to 35 U.S.C. § 365. The present application also claims priority under 35 U.S.C. § 119 from Israeli Patent Application No. IL 138322, filed Sep. 7, 2000.

BACKGROUND OF THE INVENTION

Ideally, in the field of neuro-psychology, a trained, fully qualified expert should have the opportunity to spend a substantial amount of time with each client. This time should include a significant amount of observation and testing, on a one-on-one basis. Unfortunately, there exists a chronic shortage of such professionals and, therefore, the amount of time that can be spent with each client is very limited. In addition, there is a shortage of testing materials whereby a professional can monitor the testing of each client without being physically present but nonetheless in control of the testing.

There are, in existence and in use, many types of standardized neuro-psychological tests carried out through the medium of computers; but these have a significant drawback of being generally rather static. These are so described, not simply because the contents are monotonous, but, also, because the method of application is rather rigidly implemented. Each test needs to be substantially completed before proceeding to the next without any consideration of the nature of the answers or the reactions of the client.

Furthermore, when these tests are arranged into batteries of tests, the batteries become even more static, if not positively unwieldy. The reason for this is that setting up batteries of tests is done in a standardized manner and, only after the battery of tests are substantially completed by a client, does the neuro-psychologist review the results.

It should also be explained that a testing procedure carried out under the direct supervision of an experienced and expert professional neuro-psychologist is not carried out in the static manner described, but with continuous monitoring. If the professional tester reaches conclusions prior to the end of a test, the client will be redirected to further tests, rather than be allowed to proceed with a rigid regime of testing. It would, therefore, be of substantial advantage if there existed a methodology that could construct the necessary batteries of tests, in the same manner and using the same approach, that would be utilized by a group of well qualified and expert neuro-psychologists.

Furthermore, there are a number of factors inhibiting the growth and improvements of neuro-psychological testing, most particularly because the validation of tests is extremely costly, very slow and, perhaps most important of all, very time consuming. It would be most useful if new tests and new ways of testing could easily be validated.

The problems associated with validating neuro-psychological tests are that validation must explain a correlation to known instructions, must provide results with a usably narrow distribution and, hence, the ability to decide the result.

It is not always obvious that tests are a structured means of capturing a description of how an individual performs in a given set of controlled and observable circumstances. This statement underlines the basic problem. Neuro-psychological experts are not able to invest sufficient time with each client to be able to fully perceive the full and detailed nature of each problem. Ideally, there is an important need to understand, precisely, the nature of the client and his special needs.

Therefore, it would be of significant importance and advantage, if means existed to embody the metrics from validated tests together with the expertise of time-constrained experts and bring such formed and developed tests to bear in a field so desperately in need of advancement. It would be of even greater significance, if all this could be brought to bear utilizing normal routine activities of each client.

A specific objective of every neuro-psychologist is to help clients with their normal routine activities. Because such professionals do not have the time available to, the issue of a new and highly useful methodology of testing by monitoring normal routine activities on an ongoing basis, must come to the fore.

High level certification as a neuro-psychology professional, such as a neurologist, involves a long and complex course of study and apprenticeship. Ultimately this course of study is only successfully completed by a small number of individuals. Few patients are fortunate enough to receive the full benefits that may be provided by these certified professionals, essentially because there are to few such professionals available, and their time is over subscribed by the great numbers of patients needing their help.

Today, neuro-psychology professional services are restricted to four substantially small sub-populations, of the greater population of patients, who could benefit from proper care. These sub-populations are: persons needing screening, severely disabled persons such as accident or stroke patients, extremely wealthy persons who can purchase these scarce services at any price, and substantially random small groups who happen to be "adopted" into some funded neuro-psychological research study.

Even within these groups, patients are not always able to receive optimal neurological care because of the time required for each test and its analysis, the time required to develop new tests, and the time required for the determination of the exact combination and sequence of tests to properly evaluate a given individual, which sequence may be different at each examination of the individual. Neuro-psychology professionals must spend a substantial amount of time administering tests that often yield little or no useful data. They cannot spend the vast amount of time which would enable them to observe patients in various circumstances, including routine normal activities, observation which would yield information enabling assessment of an individual's condition at a given point in time, detecting the appearance of a new condition, and perceiving the changes in and progress of a known condition.

Neuro-psychology professionals are furthermore faced with limitations in developing new tests to diagnose specific conditions more accurately or quickly, again, often because of time and cost limitations. The neuro-psychology professional has limited means available to him to validate new tests, or even to correlate information gained from the performance of routine activities by an individual under normal conditions or those experiencing changes in such conditions.

In cases when a neuro-psychology professional does develop and validate a new test, he is faced with a further problem; that of collecting payment, or royalties, for the use of the test by others.

Given these pressing circumstances, there are clearly several distinct needs in the present art. There is a need for ways and means of successfully training more persons in the complex applied-knowledge practices of clinical neuro-psychology, leading to an increase in the number of properly certified neuro-psychology professionals. Independently, there is also a need for ways and means of successfully extending the benefits of care, under the auspices of certified neuro-psychology professionals, to respectively larger populations of patients, who substantially need their help, albeit perhaps to more varying degrees than members of the four select sub-populations that are described above.

Neuro-psychology professionals undergo a long, complex and arduous course of study and apprenticeship. All too few succeed. This results in a very limited number of clients, of a potentially very large number of clients, being able to benefit from these important professionals. Unfortunately, even this small number of clients only benefit to a relatively limited degree. One of the factors that exacerbates this limit, is the availability of up-to-date and normal routine activity tests. Another factor is the limited range of conditions that will yield to the relatively out-of-date testing methods available. For the neuro-psychological professional, the development and proper validation of normal activity tests, gives rise to the difficulty of financial recovery of the costs involved as well as a return on the investment of time and substantial effort.

There is, moreover, a need to extend the level of care that a neuro-psychgology professional is able to give specific groups of patients by increasing the efficiency of the testing and observation procedures, thus enabling the observation of a patient's condition throughout the day or over an extended period of time, testing both by observation of a patient's routine normal activities and by enabling multiple or duplicate testing throughout the day. Furthermore, there is a need for a method that will enable greater efficiency in the validation of new tests and correlation of data from new tests with known parameters. Finally, there is a need for a means to enable neuro-psychological professionals to collect royalties for tests, which they have developed and which are to be used by others.

There is a distinct need in the art to allow neuro-psychologist professionals to deal with a larger number of clients and to be able to make better use of the time available. In addition, this need will be substantially enhanced if better use can be made of existing standardized tests. Add to these aspects, the development of and the ability to validate new types of tests which can fulfill all these needs whilst providing a better professional-to-client relationship with the inevitable improvement in client evaluation and treatment.

Advantages, Objects and Benefits of the Invention

Technical Issues: The present invention delivers, to individual or small groups of certified neuro-psychology professionals, an interface protocol for clinically monitoring and managing the neuro-psychological needs of very large numbers of individual patients. The preferred approach to such monitoring and testing, is within the scope of normal and routine activities. These patients are most often in need of regular testing, screening, and monitoring and, only occasionally, of referral or intervention.

Ergonomic Issues: The present invention provides a majority of patients, with regular testing, screening, and monitoring services on a "virtual-out-patient" basis by interactively delivering individually configured batteries of tests to each patient, via the Internet. These tests will include normal activity observation and monitoring. The delivery and corresponding acceptance of the testing batteries is a substantially automatically scheduled feature of the protocol of the present invention. Normal anxiety, stress and lost time of the patient, all of which are accepted and associated with prior methods of providing such testing in a clinical office setting, are all simultaneously remedied by the present invention. The present invention provides a multiplicity of services to patients in their respective daily settings, such as at home, at work, or even in transit using ordinary cellular wireless interface data-communications infrastructures as well as provides a means of accumulating a data base of normal activity testing for subsequent validation. Furthermore, certified neuro-psychology professionals using the present invention are able to provide a higher standard of ordinary care to many or even all residents of institutional facilities, such as hospitals, rehabilitation centers, and other life-care service-providing support-structures. Because of the present invention, neuro-psychology experts will become able to amass the invaluable resource of a large scale database including a means of validating normal activity testing, and thereby be able to describe new statistically validated clinical longitudinal trends and other new life-saving clinical correlations.

Economic Issues: Two fundamental economic improvements are achievable using the protocol of the present invention. Because of the present invention, patients, who otherwise might have only benefited from the neuro-psychology experts' consultation if circumstances had become life-quality critical, may now find that these services are available and affordable. Because of the present invention, neuro-psychology experts will be able to provide minimal care at low cost to a broad class of less than severely disabled persons, who have not, heretofore, had reasonable access to such services. Furthermore, because of the present invention, neuro-psychology experts will be able to modestly and efficiently conduct countless low cost neuro-psychological research studies, most especially related to normal routine activities, since such studies will become a virtual laboratory between the experts' suspicions and the reality of the data base.

Notices

Numbers, alphabetic characters, and roman symbols are designated in the following sections for convenience of explanations only, and should by no means be regarded as imposing particular order on any method steps. Likewise, the present is herein described with a certain degree of particularity. However, those versed in the art will readily appreciate that various modifications and alterations may be carried out without departing from either the spirit or scope of the present invention, as hereinafter claimed.

In describing the present invention, explanations are presented in light of currently accepted scientific, technological or medical theories and models. Such theories and models are subject to changes, both adiabatic and radical. Often these changes occur because representations for fundamental component elements are innovated, because new transformations between these elements are conceived, or because new interpretations arise for these elements or for their transformations. Furthermore, the present invention will optimistically actually contribute to changing these theories and models. Therefore, it is important to note that the present invention relates to specific technological actualization in embodiments. Accordingly, theory or model dependent explanations herein, related to these embodiments, are presented for the purpose of teaching the current man of the art or the current team of the art, how these embodiments may be substantially realized in practice. Alternative or equivalent explanations for these embodiments may neither deny nor alter their realization.

Glossary

Tests are computationally quantifiable instruments designed to assess one or more brain functions, including mental or motor functions.

A keyword that is used often in the occupational therapy world is "activities of daily living (ADLs)". ADLs are substantially concerned with the brain functions that contribute to a person's abilities to do all daily activities, including highly skilled activities. These activities include 'common tasks' such as cutting food, writing, bathing, cooking, or 'skilled' vocational tasks such as performing surgery, watch making, or serving as a corporate executive. These are things that make up the person, in his interaction with the environment. Testing relates to accessing a metric related to any elemental brain function that contributes to these tasks. These metrics may not always be related to classical "clinical neuro psychology".

Client or patient—person being tested.

Clinician or neuro-psychology professional—person prescribing or recommending the tests, such as a medical professional, a clerk in charge of vocational testing, a school social worker involved in investigating poor scholastic performance, a motor vehicles department clerk, etc.

Normal activities testing relates to testing and monitoring, whilst a client is carrying out tasks related generally to the use of communication devices and related equipment.

SUMMARY OF THE INVENTION

The present invention relates to a software driven protocol for managing a virtual clinical neuro-psychological testing program, the protocol including for each client of a plurality of clients the steps:
 a) evaluating a prior history of the client;
 b) according to the evaluated prior history, forming an appropriate battery of tests for testing the client wherein the battery incorporates pseudo-randomization of at least one representational or organizational parameter; and
 c) via a data-communications medium, interactively
   i. delivering, to the client, the formed battery of tests; and
   ii. accepting, from the client, a substantially completed response to the delivered formed battery of tests;
 d) analyzing the accepted response; and
 e) into the prior history of the client, integrating
   i. the accepted substantially completed response or
   ii. at least one analytical metric thereof.

In general, this invention relates to software setting out a set of rules whereby a clinician will be able to manage a computer operated neuro-psychological series of tests for one or more clients. This process, with a large number of clients, is started with obtaining information from each client for the purpose of assessing testing requirements. On the basis of this information, a fairly standard series of tests are typically prepared for each client which include various non-specific tests or parts of tests, randomly inserted amongst the necessary tests. These tests are then conveyed to the client through the means of a medium such as the Internet or other communications inter-connection. After the client has substantially completed the tests, these are returned to the clinician as the tests progress, to be examined in the light of the information initially supplied by the client, with the objective of establishing a measure whereby the clinician is able to determine the client's condition.

This procedure enables the neuro-psychologist to format tests and then, while monitoring each test and continuously having evaluated the results, by means of any one of a number of communication devices, to set further tests to more closely determine the client's situation without having to expend time in personal attendance on the client. Randomly inserted and apparently irrelevant tests have two major purposes. Firstly, they represent a means of interrupting the monotony of a series of similar tests and secondly, these tests will provide a means for developing additional tests for assessment and validation so that the scope of testing is constantly being expanded.

Advantages to such a system and improvements to existing procedures is excitingly significant. Professional neuro-psychologists will be in a position to monitor many more clients, more frequently and more thoroughly, whilst simultaneously making a major advance in expanding the library of validated tests.

Furthermore, the present invention relates to a clinical protocol for normal-use activities, the protocol including the steps of:
 a) for substantially each client in an ensemble of clients, monitoring at least one metric of normal-use activities;
 b) for substantially each metric of the at least one metric of normal use activities, until a predetermined threshold of validation is achieved for an ensemble of clients, first, managing a virtual clinical neuro-psychological testing program for substantially each client in the ensemble; and correlating analytical metrics derived from the neuro-psychological testing program with the monitored metrics of normal-use activities, thereby validating at least one of the monitored metrics of normal-use activities as a neuro-psychological metric; and
 c) for substantially each validated metric of the at least one metric of normal use activities, second, managing a virtual clinical neuro-psychological testing program for at least one client wherein a validated normal-use activity metric is used as a classical testing instrument.

In general the present invention also provides a means for developing testing procedures related to normal activities, generally with regard to each of a number of clients' interactions with a computer or other communication device. Appropriate software enables the clinician to record and later compare measurements derived from these normal activities. This software provides the means for validating this normal activity testing. Such validated series of normal activity tests provide the means, then, to utilize these validated normal activity tests on a client.

The procedure described, enables a clinician to develop new validated forms of testing whilst conducting existing forms of tests without being physically present with the client. The usefulness of these newly validated tests, involving normal activities, cannot be over-emphasized in the light of the present lack of normal activity validated tests. Clearly the optimum and preferred method of testing would be direct observation, on a continuous basis, of normal activities by a client. Monitoring normal activities and evaluating the client on the basis of validated normal activity tests as outlined in the protocol described above could supercede lengthy direct, one-on-one observation.

It should be understood that this aspect of the present invention, though quite similar to the previous aspect, has some intrinsically significant differences. The utopian concept of professional neuro-psychologists being able to spend almost limitless time observing client normal activity behavior, comes a step closer with an increase in the available arsenal of testing materials. Also, tests can be formed and applied that are specific in terms of each client's needs to a substantially larger number of clients and developed as normal activity tests rather than presently available rigid standard test batteries.

Notwithstanding the above, the present invention also relates to a software driven protocol for managing a virtual clinical neuro-psychological dynamic hierarchical testing program, the protocol including for each client of a plurality of clients the steps:

a) evaluating a prior history of the client;
b) according to the evaluated prior history,
  i. interactively forming an appropriate battery of tests for testing the client wherein the battery incorporates pseudo-randomization of at least one representational or organizational parameter;
  ii. via a data-communications medium, interactively delivering, to the client, the formed battery of tests;
  iii. accepting, from the client, a substantially completed response to the delivered formed battery of tests;
  iv. analyzing the accepted response; and
  v. returning to step b)i until complete; and
c) into the prior history of the client, integrating
  i. the accepted substantially completed response or
  ii. at least one analytical metric thereof.

In general this procedure for testing differs from the initially described procedure. At present, the initial procedure utilizes a selection of a battery of tests transmitted to a client. After a substantially completed battery of tests is returned for evaluation, analyzed results are integrated into the historical information originally supplied by the client. This initially described procedure has a significant drawback, in that the whole structure of testing is inflexible and totally rigid in that completed tests are evaluated only subsequent to the client returning these. Generally, no provision is presently made for progressive monitoring of results, emanating from ongoing tests.

The procedure, described here, makes provision for avoiding this pitfall.

A battery of tests is selected by a neuro-psychologist as is the present practice. As the tests progress, from the continuous stream of results, the clinician is able to evaluate results as a continuum and can withdraw the running test, even mid-test. Substitute alternative tests are then introduced that will give a better insight into the client's situation as well as the means for deriving a narrower distribution of results. This dynamic process of replacing ongoing tests, in a hierarchical way, may be repeated as often a necessary to achieve better and more specific results. Again, a specific stress is laid on the use of collecting and collating the results of the normal activity tests, concurrent with the above process. These normal activity results are then validated to provide normal activity testing facilities for use on clients.

Present conventions of neuro-psychological testing limit professionals to a small number of clients, who can only be monitored for a very limited amount of time, as opposed to the improvements that this dynamic hierarchical protocol envisages. More appropriate use can be made of a wider range of tests available from the usage of normal activity testing as well as the ability to monitor many more clients by means of communication devices. Most significant is the avoidance of the rigidity of existing testing methods insofar as tests envisaged in these aspects of the present invention, allow for a continuous interchange of results and tests between client and professional via the communication medium, enabling the professional dynamically to vary and to guide the tests hierarchically, to obtain results that will be more specific to the client's situation.

An additional aspect of the present invention relates to a software driven protocol for managing a virtual clinical neuro-psychological testing program based on normal use activities, the protocol including for each client of a plurality of clients the steps:

a) evaluating a prior history of the client;
b) according to the evaluated prior history, forming at least one normal use activity factor of tests for testing the client wherein said at least one normal use activity factor incorporates pseudo-randomization of at least one representational or organizational parameter; and
c) via a data-communications medium, interactively
  i. delivering the formed at least one normal use activity factor tests to the client;
  ii. the client substantially completing the normal use activity factor tests; and
  iii. accepting, from the client, a substantially completed response to the delivered normal use activity factor tests;
d) analyzing the accepted response; and
e) into the prior history of the client, integrating
  i. the accepted substantially completed response or
  ii. at least one analytical metric thereof.

In general, the invention also defines a procedure for carrying out testing procedures elaborated in the earlier parts of this description, but in this instance, the tests are built up, in a progressive manner, using the concept of previously validated normal activities testing.

Again, the neuro-psychologist specifies a software driven battery of tests. Again, the inclusion of apparently non-specific tests interspersed amongst the other tests is carried out to provide the client with a rest from the rigors of the ongoing testing as well as providing additional test information for later validation. Tests are conveyed to the clients through the means of a communications medium using a computer system or other personal communication device and, while being substantially completed, are returned to the clinician for recording, collating, contrasting and inclusion with the earlier recorded history of the client. It is stressed that this entire procedure relates to validation of and subsequent use of normal activities testing. This then is the optimal and preferred way of testing clients, without the continuous participation of the professional neuro-psychologist in attendance with each separate client and without the client being subjected to presently utilized lengthy, generally rigid and often monotonous tests.

In addition, the insertion of randomly placed and apparently inconsequential tests into each of the above test procedures, apart from breaking the monotony of testing, provides a means for developing new, innovative and perhaps novel, forms of neuro-psychological testing. Clearly, validation of these newly developed tests is a natural corollary to all of the above.

The ideal way for professional neuro-psychologists to carry out testing is to expend large amounts of time monitoring each individual client within the framework of normal and routine activities. This is not really possible when considering the lack of sufficient qualified professional experts. There are many aspects to the present invention that will emulate this idyllic scenario. Not only will the scope of each professional be expanded in terms of the number of clients who can be simultaneously monitored, but this monitoring will be in the context of normal activities testing. In addition, the scope of testing facilities will be expanded on an ongoing basis, as a consequence of the use of pseudo randomly incorporating normal activity tests.

The major thrust of this invention, is the development of a broad spectrum of innovative test methods, which will provide the professional neuro-psychologist with the means of dealing with substantial numbers of clients without the need to expend long hours of direct contact with clients. Professionals will also be giving a much higher quality of service to these clients. Most significant is the use of normal activities testing through the medium of commonly used communication devices.

To summarize, there is a specific problem that presently exists. Expert, professional neuro psychologists are unable to cope with the existing work load of clients requiring direct, continuous and long term monitoring in terms of their normal routine activities, especially using the generally rigid types of testing batteries available. The present invention provides a means of overcoming all these problems. Clients can be monitored directly on a continuous and interactive basis via communication media during performance of their normal routine activities, with the professional having the means to vary testing procedures as the pattern of client tests indicates a direction for achieving more direct and narrower results, specific to each client's needs. Finally, the professional will be able to so monitor substantially larger numbers of clients, using these much improved and validated test methods. Validation of testing methods will naturally follow this new scenario, producing a much broader and improved scope for the professional neuro psychologist.

BRIEF DESCRIPTION OF THE FIGURES

In order to understand the invention and to see how it may be carried out in practice, embodiments including the preferred embodiment will now be described, by way of non-limiting example only, with reference to the accompanying drawings, in which.

DETAILED DESCRIPTION OF THE INVENTION

There are several aspects to the present invention. Using the present invention, the professional neuro-psychologist will be able to manage a large number of clients on a professional basis and to utilize a system and a method to influence creation of batteries of tests and evaluation parameters. This will provide the means to evaluate a client using up-to-date instruments. Monitoring clients or a specific condition in a client, through a battery of tests, will be done using a procedure, which will enable direct and ongoing contact between client and clinician, as necessary.

A substantial portion of the tests can be administered, evaluated, and monitored automatically. Ongoing results fed back on an on-line basis will be evaluated to determine the need for further testing and the nature of such testing. This automated process further provides the neuro-psychology professional with new parameters and evaluative metrics for determining and assessing a neuro-psychological condition in a client.

Furthermore, maintaining and improving a professional neuro-psychologist's ability to manage a large client base with an appropriate level of professional service, is an essential factor of this invention. Each client requiring testing, will have the benefits of paying for actual services received, having access to a multiplicity of tests, have access to all appropriate professionals and a reduced burden of testing.

However, it must be stated, that it is a specific desire of the neuro-psychology professional, to subject clients to as little testing as possible whilst obtaining a satisfactory diagnosis or reaching an accurate conclusion. The interests of the client are best served by being subjected to a minimum burden of stress, trauma, anxiety or simple bother, during the testing procedure.

Figure 1:
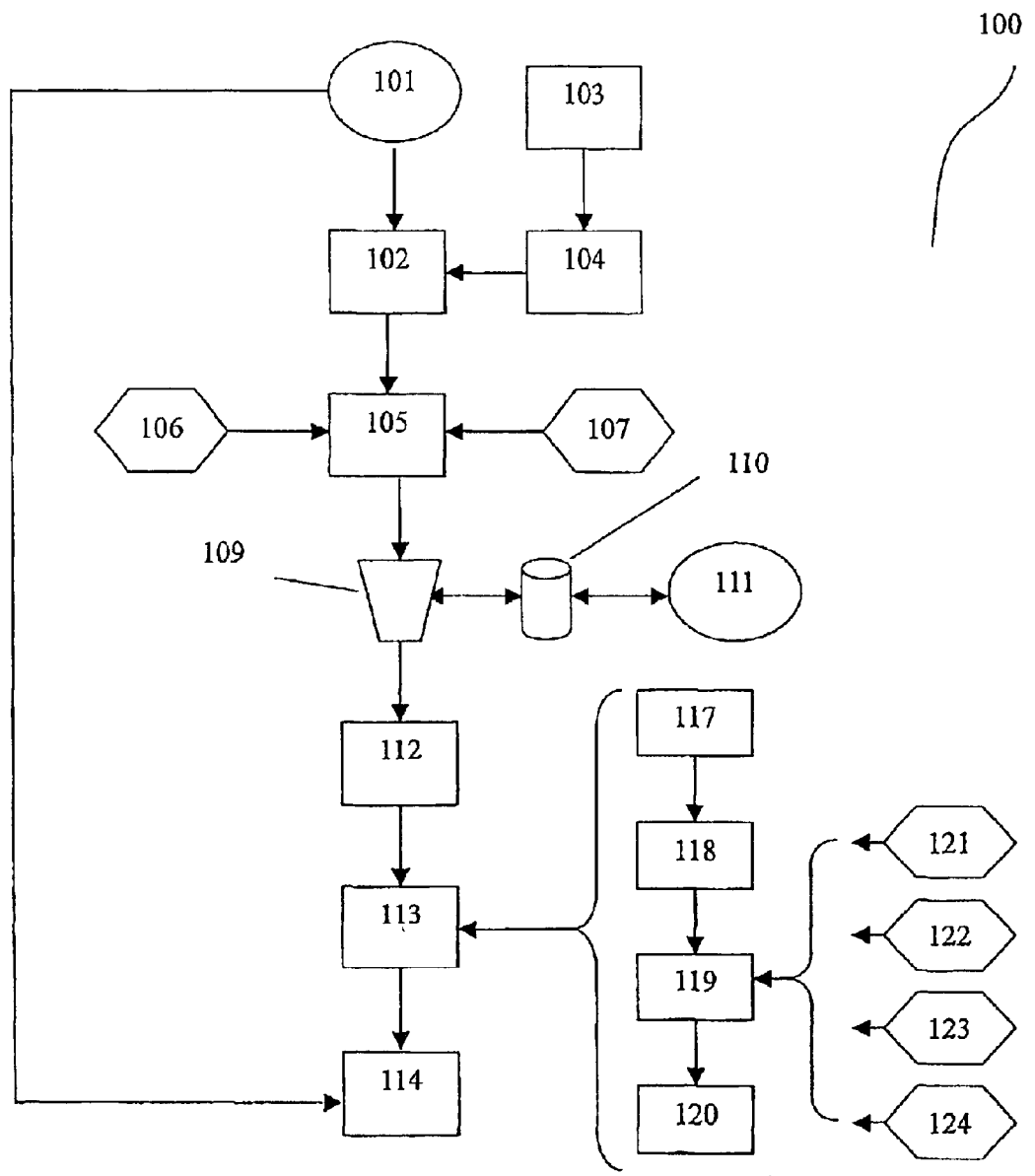
FIG. 1 illustrates a schematic view characterizing the steps of a software-driven protocol for managing a virtual clinical neuro-psychological testing program.

Reference is now made to FIG. 1, which illustrates a schematic view characterizing the steps of a software-driven protocol (100) for managing a virtual clinical neuro-psychological testing program.

The present invention relates to a software-driven protocol for managing a virtual clinical neuro-psychological testing program, the protocol including for each client of a plurality of clients the steps:

a) evaluating (102) a prior history (101) of the client;
b) according to the evaluated prior history, forming (105) an appropriate battery of tests (106) for testing the client wherein said battery incorporates pseudo-randomization (107) of at least one representational or organizational parameter; and
c) via a data-communications medium (110), interactively
   i. delivering (109), to the client (111), the formed battery of tests, and
   ii. accepting (112), from the client, a substantially completed response to the delivered formed battery of tests;
d) analyzing (113) the accepted response; and
e) into the prior history of the client, integrating (114)
   i. the accepted substantially completed response, or
   ii. at least one analytical metric thereof.

Each of a multiplicity of clients will be provided with specific software, which will enable a professional clinician to maintain an interchange of information using corresponding software. This will allow a client to feed historical information to the clinician, receive testing procedures and instructions, carry out tests and convey results to the clinician for evaluation and integration into a client's history in order to determine further testing requirements or to draw conclusions regarding each client's situation.

Simply stated, evaluating a prior history of the client is a clinician's placing an emphasis on automatic determination of the tests needed based on the history of a client or, alternatively, a clinician shifting the emphasis to a higher level of involvement in the progress of the client.

More specifically, forming an appropriate battery of tests, is the consequence of a clinician's evaluation of the condition of a client. Such a battery of tests will comprise a variety of tests including arranging some of the above-mentioned representational or organizational parameters in a random manner. The reason for applying a random rearrangement, revolves around the problem that clients tend to learn tests and, consequently, these no longer measure what was intended or required. To avoid this problem it is important that tests are not repeated at respective known close intervals. Simply stated, re-use of the same testing instrument is generally restricted according to the protocol that validated that instrument. Nonetheless, randomization may be accomplished by changing the order of elements in a test or by changing around actual examples in any question. Introducing these different levels of changes ensures maintaining the efficacy of using repeated testing instruments at appropriate intervals.

Initially, the tests that are formed into a battery, will be appropriate to the client's evaluated situation. Using a data communications medium (110) interactively, implies sending test materials to a client and receiving the substantially complete results from the client. The cycle of sending and receiving may occur as a single or as a series of interchanges, when administering a single battery. It is preferred that the remainder of the formed battery is modified after each interchange cycle; as will be described in detail below in the section describing dynamic hierarchical testing.

Morespecifically, delivering to the client, the formed battery of tests, takes the form of conveying testing instruments by means, for example, of the Internet, by email or other data communication media. Similarly, accepting from the client, will also take place using one of similar data communication media.

Analyzing the accepted response from the client, more specifically, is the means by which a clinician will decide on comparing accepted results to normal or anticipated standards and then to decide whether to call in a physician or to deliver a further battery of tests. Further, by integrating these analyzed results into the prior history of the patient, the clinician becomes able to more easily determine the route to be followed, in particular, with regard to further testing, if needed. Subsequently scheduled tests, more specific to a client's condition or need, will be applied, following on a defining of the current forming of a battery of tests to the next forming event and so to evaluate results.

To conclude, the cycle of events defined by the present invention, enables the fulfillment of the broad goals of the present invention. A professional can deal with a large client population and the client will be minimally subjected to invasive interaction with the professional.

More sophisticated varieties of the present invention, described below, will more efficiently make use of the professional's time and more efficiently reduce the client's burden, without reducing the efficiency of interaction between professional and client.

When performed by an expert, a standard neuro-psychological evaluation involves using a loosely structured battery of substantially standardized tests, that are progressively individualized to specific diagnostic issues of each particular patient. Hence, the expert forms and then uses a custom configured battery of tests that provide a thorough investigation of a patient, depending on the circumstances of the problem and the state of the patient.

Sometimes, a rapid screening examination may be adequate if the problem is minor or intermittent. On the other hand, screening may be all that is possible if the condition or participation of the patient does not allow more detailed testing. If certain domains of function are suspected to be abnormal, based on historical information or on positive findings during screening tests, then more detailed testing of those domains is warranted.

It is apparent that the neuro-psychological professional will be able to manage a larger number of clients using tools supplied by a broad range of experts. Simultaneously, billing and time management will be superior. On the other hand, clients will receive a more cost-effective and professional service, and have the benefit of a significantly reduced testing burden.

According to an embodiment of the present invention, the protocol in which analyzing the accepted response includes: applying (119) rule-based criteria for quantifying (120) at least one difference between a pair of metrics selected from the list:
  a) the evaluated prior history (121) of the client;
  b) a metric of expected performance (122) on at least one test of the formed battery of tests;
  c) actual performance (123) on at least one test of the formed battery of tests; and
  d) normative values (124) based on large body of data for at least one test of the formed battery of tests.

More specifically, results will be evaluated and applied to a selection of additional tests, if required, by comparing two of the metrics, evaluated prior history, a measure of expected performance, actual performance and normal performance from a body of previously developed data. This enables a system embodying the present method to determine whether the next level of interaction of tests is warranted.

A comparison of the evaluated prior history of a client with a metric of expected performance will indicate whether the selected battery of tests is likely to be appropriate. Comparing the evaluated prior history with a metric of actual performance will enable the clinician to determine the subsequent course of action, namely to apply further, more specific testing instruments, to call in the services of a physician or to decide that no further testing is indicated at the present time. Comparing the evaluated history with normative test values, based on a large body of data, enables the clinician to anticipate testing results so that he can preempt the need for the client to carry the testing instrument to its conclusion or to replace the test with another, more appropriate or to decide that no further testing is indicated at the present time.

Further, to compare a metric of expected performance with actual performance, confirms, for the clinician, the correct direction of, and the appropriateness of the selected testing instruments. Also, comparing the expected performance with normative values for a metric of the same test enables the clinician to determine the nature of the condition of the client, relative to the norm, in the light of the evaluated history of the client. Finally, comparing actual performance against normative values, gives the clinician an insight into the nature of the condition of the client and to decide whether further specific testing is called for or whether consultation with other expert professionals is indicated.

Figure 2:
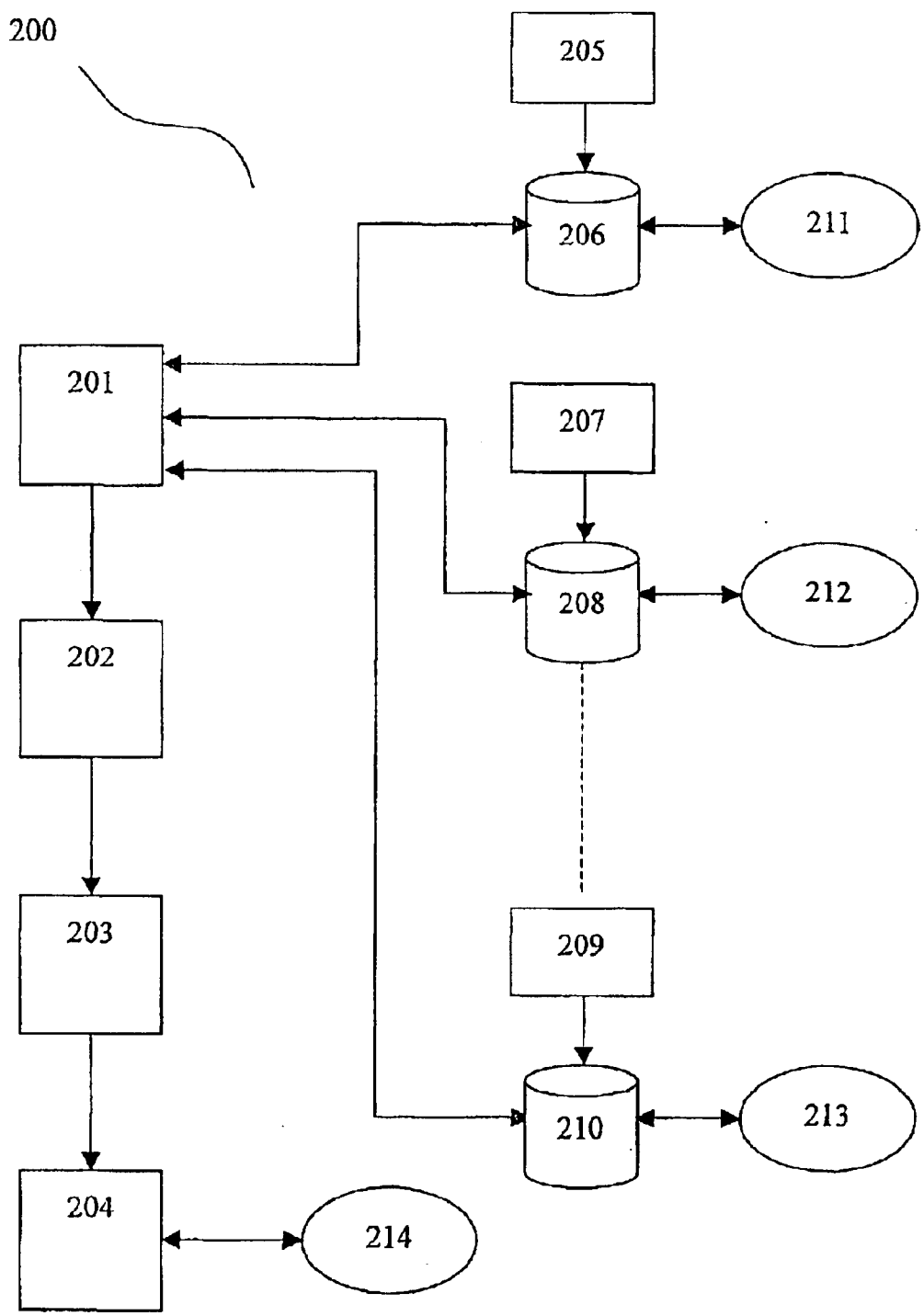
FIG. 2 illustrates a schematic view characterizing the steps of a clinical protocol for normal use activities.

Reference is now made to FIG. 2 which illustrates a schematic view characterizing the steps of a clinical protocol (200) for normal use activities, the present invention also relates to a clinical protocol for normal-use activities, the protocol including the steps of:
  a) for substantially each client in an ensemble of clients (211, 212, 213, etc.) monitoring (201) at least one metric of normal-use activities;
  b) for substantially each metric of the at least one metric of normal use activities, until a predetermined threshold of validation is achieved for an ensemble of clients, first managing (202) a virtual clinical neuro-psychological testing program (205, 207, 209, etc.) for substantially each client in the ensemble, and correlating (203) analytical metrics derived from the neuro-psychological testing program with the monitored metrics of normal-use activities, thereby validating at least one of the monitored metrics of normal-use activities as a neuro-psychological metric; and
  c) for substantially each validated metric of the at least one metric of normal use activities, second managing (204) a virtual clinical neuro-psychological testing program for at least one client (214) wherein a validated normal-use activity metric is used as a classical testing instrument.

More specifically, second managing applies to using the technique of using validated normal activities testing. In particular, what has been learned about normal activities, contributes to the way clients' testing programs are managed.

Current practice requires the clinician to administer a neuro-psychological test, substantially, in the form in which the test was validated. Generally, this involves many repetitions over extensive testing sessions. There are currently no validated automated models for making decisions regarding test termination or switching to a different test during the course of the testing session. To partially alleviate this burden on the client, the concept of normal activities testing is introduced.

More specifically, software will provide a means for monitoring a large number of clients during respective normal activities (206, 208, 210, etc.) managing each client until a sufficient level of validation is achieved by correlating results, and then allowing evaluation of clients' normal activity use with the validated test.

Of necessity, the optimal method of monitoring such normal activities testing, is supplemented with direct on-line testing. This would seem to require a reduced level of apparent participation by a client and, therefore, substantially less trauma and stress for a client. Simultaneously, the clinician is able to deal with a plurality of clients improving the time efficiency and hence the cost effectiveness of such testing.

Figure 3:
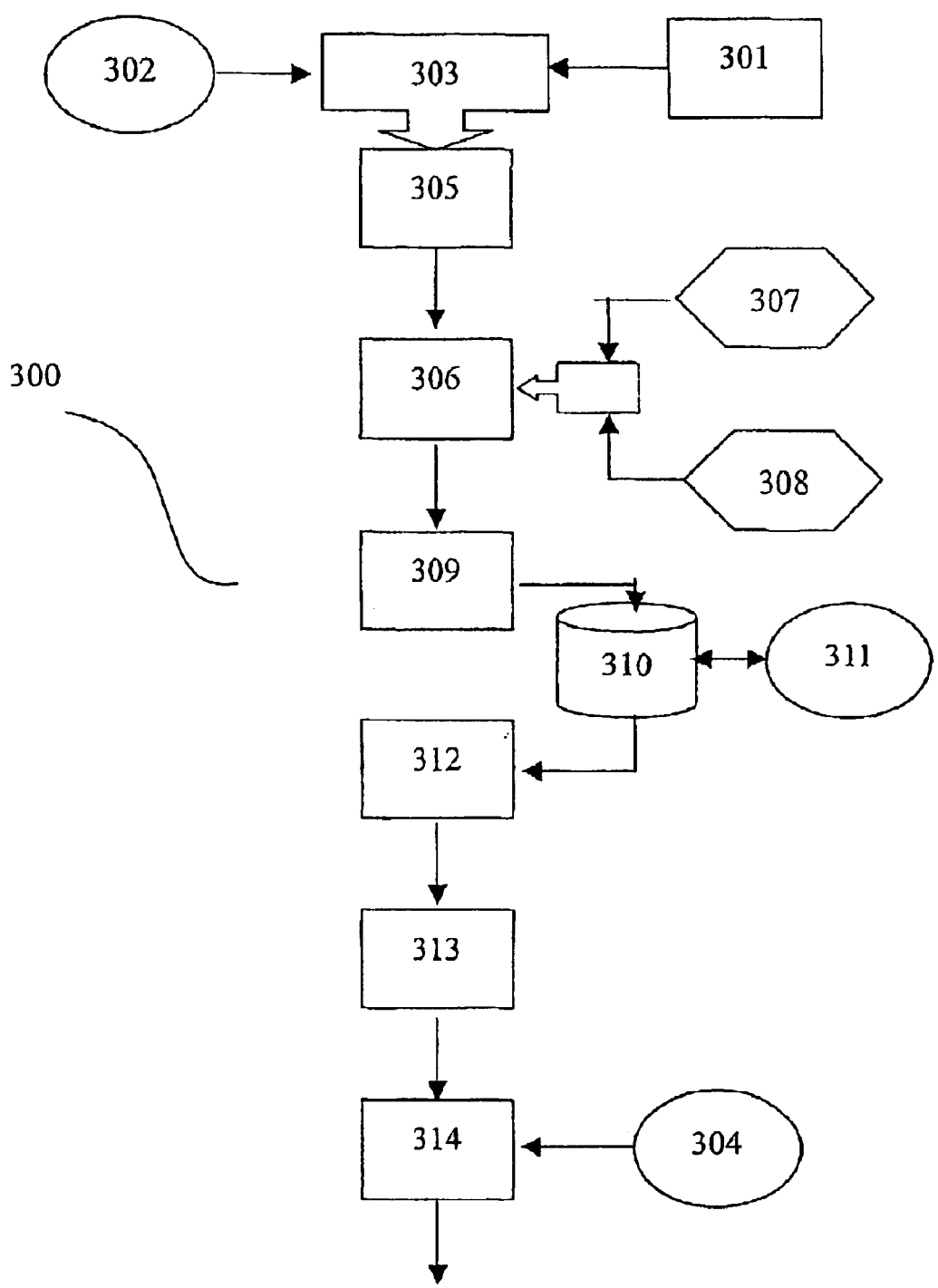
FIG. 3 illustrates a schematic view characterizing the steps corresponding to first managing and second managing in the clinical protocol for normal use activities.
Figure 9:
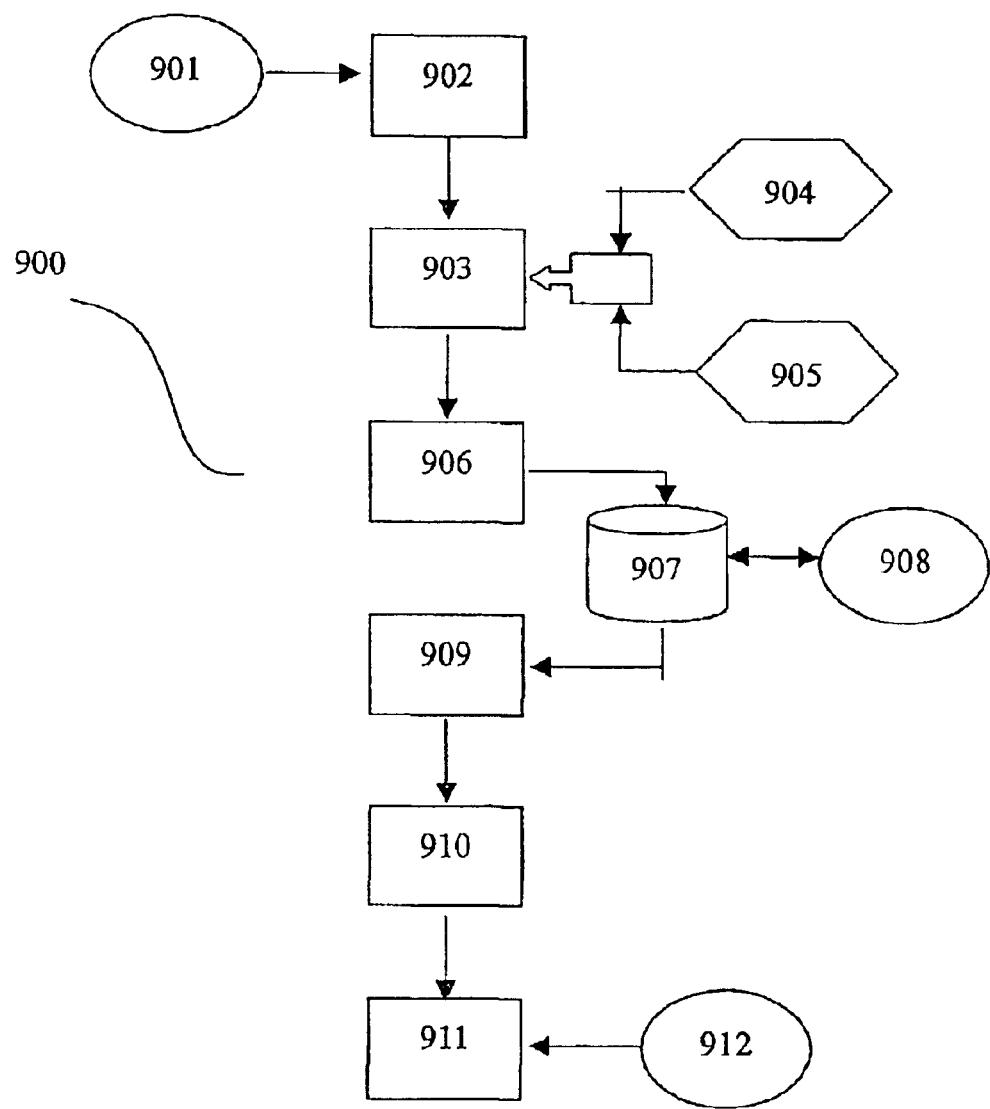
FIG. 9 illustrates a schematic view characterizing the steps of first managing and second managing in the protocol for validating a non-validated test in a formed battery of validated tests by correlating responses from the validated and non-validated tests.

FIG. 3 illustrates a schematic view characterizing the steps corresponding to first managing and second managing (300) in the clinical protocol for normal use activities. In addition, FIG. 9 illustrates a schematic view characterizing the steps of first managing and second managing (900) in the protocol for validating a non-validated test in a formed battery of validated tests by correlating responses from the validated and non-validated tests.

According to a further embodiment of the present invention, the clinical protocol for normal-use activities in which occur first managing and second managing, include the steps:
  a) evaluating (305) or (902), a prior history (302) or (901) of the client;
  b) according to the evaluated prior history, forming (306) or (903) an appropriate battery of tests (307) or (904) for testing the client wherein said battery incorporates pseudo-randomization (308) or (905) of at least one representational or organizational parameter; and
  c) via a data-communications medium (310) or (907), interactively
    i. delivering (309) or (906), to the client (311) or (908), the formed battery of tests; and
    ii. accepting (312) or (909), from the client, a substantially completed response to the delivered formed battery of tests;
  d) analyzing (313) or (910) the accepted response; and
  e) into the prior history (302) or (912) of the client, integrating (314) or (911)
    i. the accepted substantially completed response or
    ii. at least one analytical metric thereof.

According to a subsequent embodiment of the present invention, the clinical protocol for a metric of normal use activity of the monitored at least one metric of normal use activities, is calculated by measuring an activity selected from the list of copying, printing, pasting, editing, inserting, formatting, exchanging tasks, web surfing, backspacing, deleting and shifting, substantially, as described earlier I DON'T SEE ANY OF THIS REFERENCED EARLIER in the examples of making use of personal computers, palm-held computers, cellular telephones, etc.

It is reasonable to presume, once systems are operated according to the present invention, other normal activity monitoring devices will become standard items requested by clinicians for the routine administration of their clients. These could include devices such as a telemetric neurology monitor, a telemetric heartbeat monitor, etc.

Figure 4:
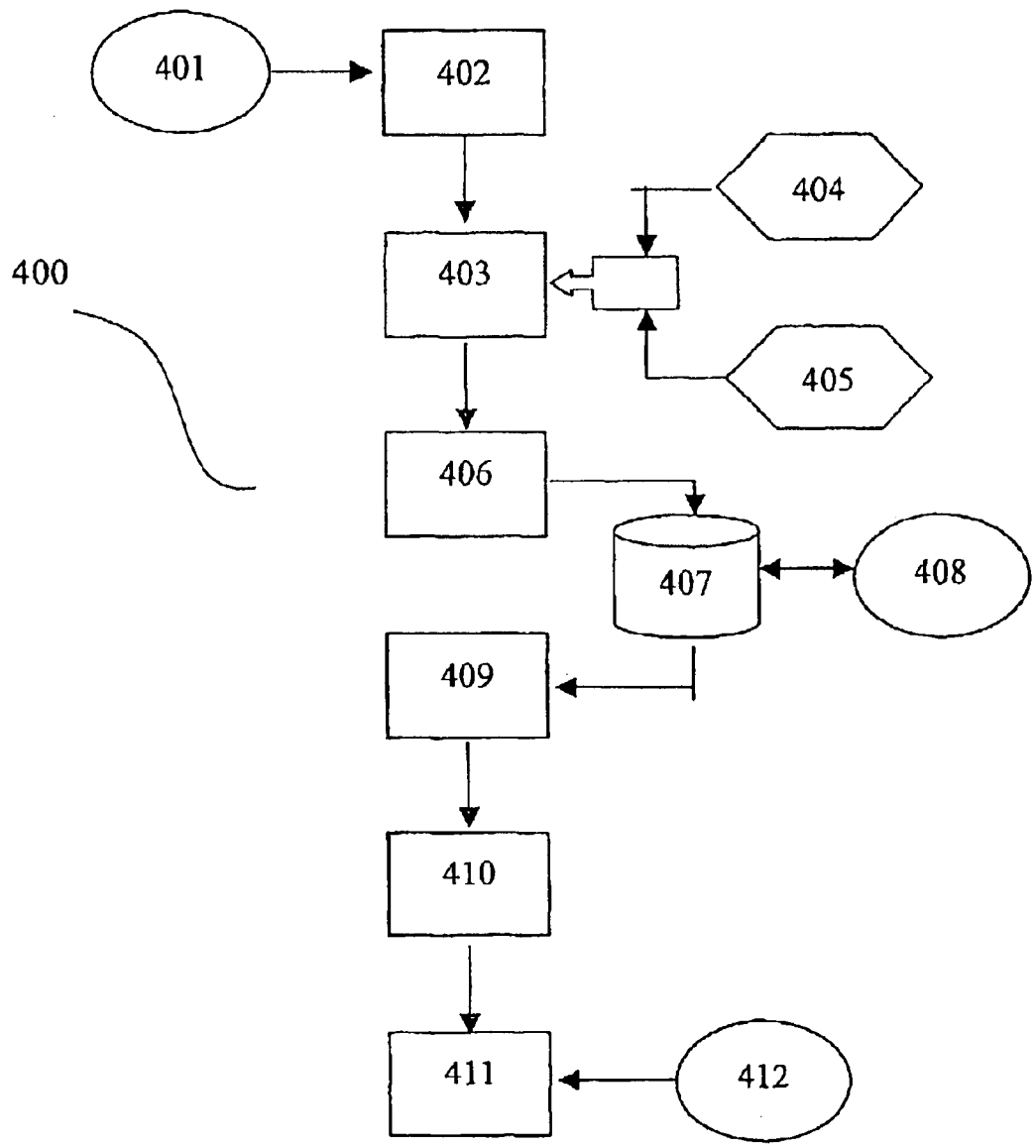
FIG. 4 illustrates a schematic view characterizing the steps corresponding to first managing and second managing in the clinical protocol for validating a new testing instrument.

Reference is now made to FIG. 4, this illustrates a schematic view characterizing the steps corresponding to first managing and second managing (400) in the clinical protocol for validating a new testing instrument, according to an additional embodiment of the present invention, The clinical protocol for validating a new testing instrument, that describes first managing and second managing include the steps:

a) evaluating (402) a prior history (401) of the client;
b) according to the evaluated prior history, forming (403) an appropriate battery of tests (404) for testing the client wherein said battery incorporates pseudo-randomization (405) of at least one representational or organizational parameter; and
c) via a data-communications medium (407), interactively
  i. delivering (406) to the client (408), the formed battery of tests, and
  ii. accepting (409), from the client, a substantially completed response to the delivered formed battery of tests;
d) analyzing (410) the accepted response; and
e) into the prior history (412) of the client, integrating (411)
  i. the accepted substantially completed response or
  ii. at least one analytical metric thereof.

There is apparent repetition of aspects and certain embodiments of the present invention but this is necessitated due to differences in emphasis. In the particular case, regarding validating a new testing instrument that has been dealt with, the emphasis has changed from managing a testing program of validated testing instruments to using normal activities as part of the measure and validation of this form of testing. Particularly, managing a testing program containing validated testing instruments, and using normal activities as part of the validation of normal use activities, will replace some of the known validated testing instruments.

Validation of neuro-psychological tests is presently a cumbersome and extremely costly procedure. Clinicians are required to administer tests in the form in which these were validated. Therefore, development of normal activity testing procedures as well as the introduction of validation techniques for these procedures, will enable a clinician to fulfill this criterion at minimal cost and with a minimum of direct effort.

More specifically, the effects of the utilization of such a testing procedure on the client are manifold. Inevitably, present testing procedures cause stress and trauma and, in many instances, render little or no useful results, whereas normal activities testing should be virtually free of such problems. With the present invention, the client will have a benefit of expertise from a multitude of professionals in many connected fields. Another significant factor will certainly relate to substantially reduced costs.

Figure 5:
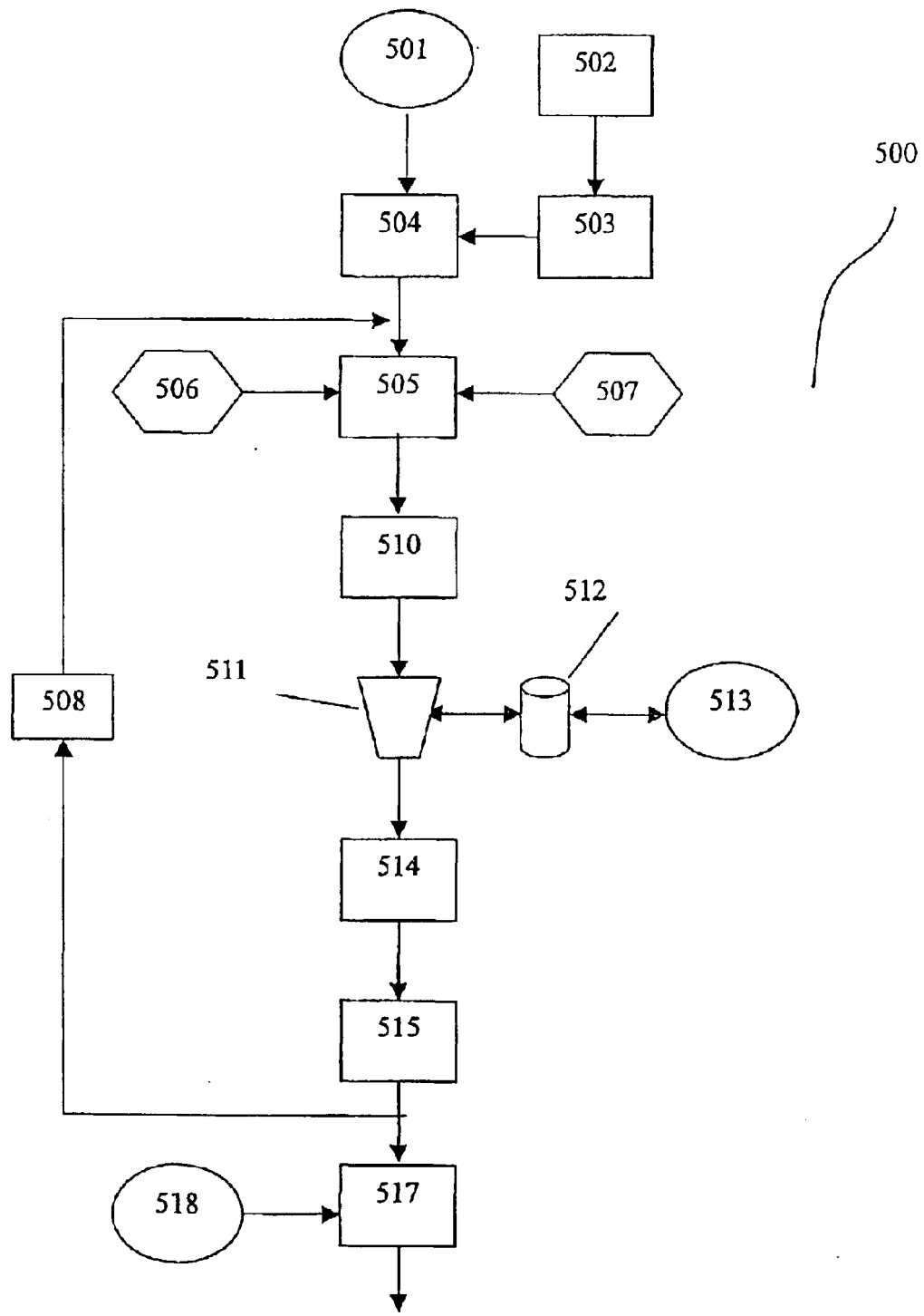
FIG. 5 illustrates a schematic view characterizing the steps of a software driven protocol for managing a virtual clinical neuro-psychological dynamic hierarchical testing program.

FIG. 5 illustrates a schematic view characterizing the steps of a software driven protocol (500) for managing a virtual clinical neuro-psychological dynamic hierarchical testing program.

The present invention further relates to a software-driven protocol for managing a virtual clinical neuro-psychological dynamic hierarchical testing program, the protocol including for each client of a plurality of clients the steps:

a) evaluating (504) a prior history (501) of the client;
b) according to the evaluated prior history,
  i. interactively forming (505) an appropriate battery of tests (506) for testing the client wherein said battery incorporates pseudo-randomization (507) of at least one representational or organizational parameter;
  ii. via a data-communications medium (511), interactively (512) delivering (510), to the client (513), the formed battery of tests,
  iii. accepting (514), from the client, a substantially completed response to the delivered formed battery of tests;
  iv. analyzing (515) the accepted response; and
  v. returning (508) to step b)i until complete; and
c) into the prior history (518) of the client, integrating (517)
  i. the accepted substantially completed response or
  ii. at least one analytical metric thereof.

Simply stated, evaluating a prior history of the client, includes determining the basis on which a battery of tests will be constructed to test specific aspects regarding the client. Further, forming this appropriate battery of tests incorporating pseudo-randomization, is specifically for the purpose of ensuring that repeating these tests at a later time, will prevent the client from learning to perform the tests and thus, defeat the objective of the tests. In addition, delivering these formed batteries of tests and later accepting the substantially completed tests, using a data communication medium, facilitates accomplishing the purpose of interactively analyzing the test results and of delivering additional or more specific tests. This cycle of evaluating, forming tests, delivering and accepting these tests, and analyzing the results, is repeated until the clinician is satisfied with the results. Integrating these into the prior history of the client, to determine the course to be followed with respect to the client, will assist in deciding whether further testing or whether consultation with other experts is needed.

Once again apparent repetition of aspects and certain embodiments of the present invention is necessitated due to differences in emphasis. In the particular case that has been dealt with, relating to a software-driven protocol for managing a virtual clinical neuro-psychological dynamic hierarchical testing program, the emphasis has changed from managing a testing program and from validation of normal activities testing, to managing a virtual clinical neuro-psychological dynamic hierarchical testing program.

More specifically, managing a virtual clinical neuro-psychological dynamic hierarchical testing program, implies allowing testing programs to proceed only to a point at which the result will permit a better or more specific test or battery of tests to be applied. This will occur without the client having to, necessarily, complete the originally formed battery of tests.

There are currently no validated automated models for making decisions regarding test termination or test switching during the course of a testing session. Embodied in the present invention is a means for using a model whereby performance of neuro-psychological tests is evaluated on-line. An automated decision process is used to determine one of several options, including continuation of the test, premature termination of the test, change in level of difficulty of the same test, or switching to another test.

For example, for each level of difficulty for each test, an upper and lower boundary form the range of sensitivity for performance at that level. Performance may be determined abnormal for that level based on predetermined values of certain performance parameters in relation to said boundaries. Decisions to terminate the test on the basis of poor validity may be based on indices indicative of poor cooperation with the test instructions or of fictitious results from malingering (using known techniques to detect inconsistencies in the results). Tests may be terminated based on general poor performance signifying severe general cognitive dysfunction, or poor performance in specific domains signifying focal deficits worthy of more focused testing.

Within a given test, a hierarchical design is used to move the test through different levels of difficulty. This is accomplished, for different types of tests, by utilizing the principles of utilizing a series of tests having changing levels of difficulty. These are:

a) Screening for subtle deficits may be accomplished by starting at the level of difficulty expected for normal individuals. If performance is in the range of normal, then the test is terminated. If there is abnormal performance, the test is repeated at a lower level of difficulty, until satisfactory performance is accomplished. For example, the common eye chart exam for visual acuity may be administered as a screening test by starting with the smallest letters. If the subject reads the lowest line satisfactorily, the exam is terminated. If not, the subject is presented with a line of larger letters until he is able to read the letters satisfactorily.

b) When seeking the highest level of performance, such as in vocational testing, the level of difficulty may start with that of average performance and may gradually increase until performance becomes inadequate or abnormal.

c) When quantification of the performance is required, such as in patient longitudinal follow-up during a drug rehabilitation or therapeutic program, the level of difficulty may start at the subject's previous level of performance and either increase or decrease depending on the performance.

Decisions to switch to other tests within the prescribed battery or to tests outside of the original battery may be made based on test performance measured on-line:

a) If enough information has been garnered from a given test to determine whether performance is normal or, alternatively, to determine the degree of abnormality, a decision may be made to move to the next test in the given pre-determined battery.

b) If a specific domain of abnormality has been identified, a decision may be made to switch to one or more test that further expand upon the area(s) of abnormality.

Figure 6:
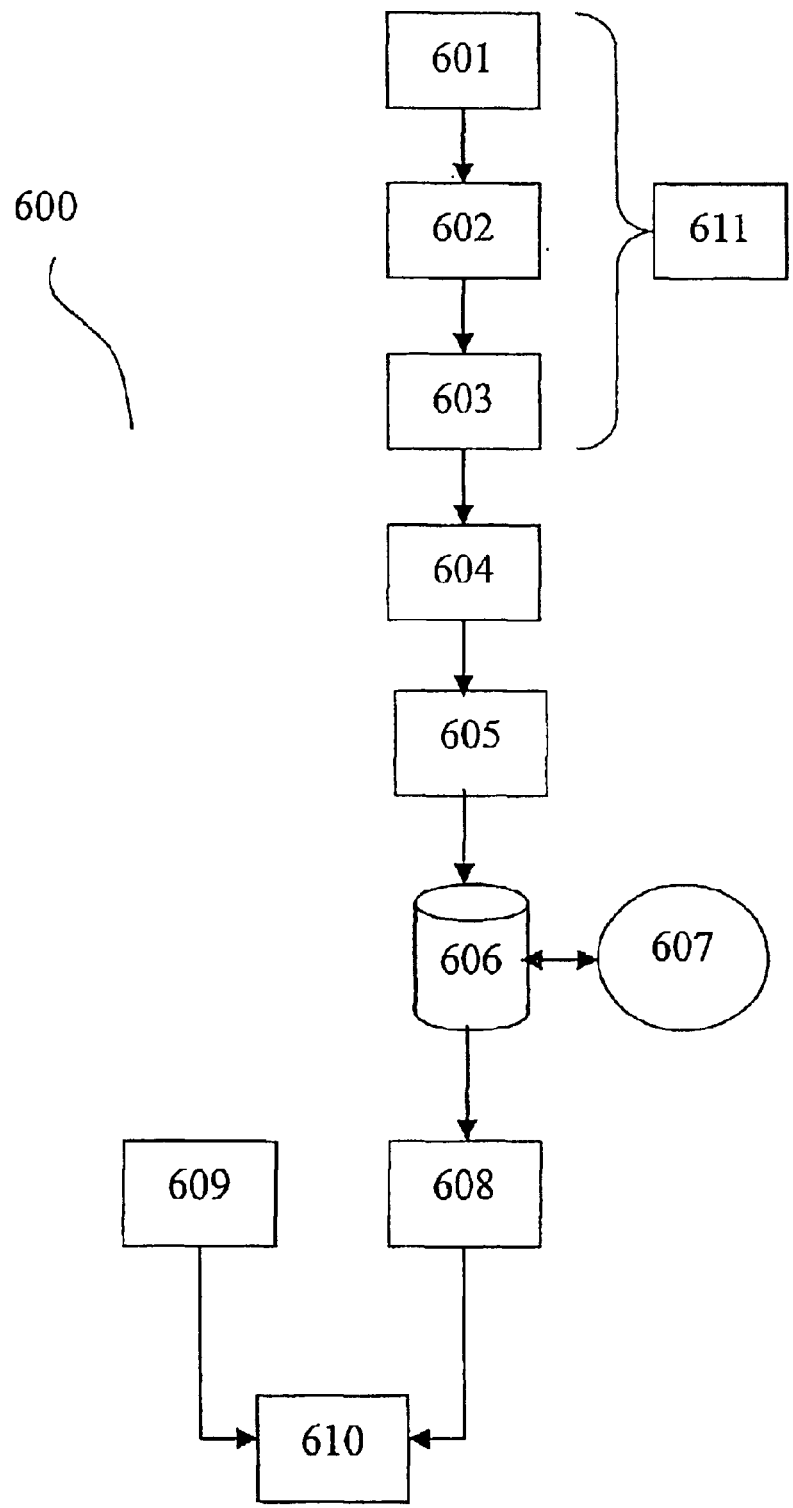
FIG. 6 illustrates a schematic view characterizing the steps of the protocol for validating a non-validated test in a formed battery of validated tests by correlating responses from the validated and non-validated tests.

FIG. 6 illustrates a schematic view characterizing the steps of the protocol (600) for validating a non-validated test in a formed battery of validated tests by correlating responses from the validated and non-validated tests.

According to another embodiment of the present invention, the protocol (600) further includes the steps of:

a) Establishing (601), upgrading (602) and maintaining (603) as appropriate, a validity metric (611) for a substantially non-validated test (604), for each client (607) of an ensemble of clients;

b) introducing (605) a substantially non-validated test into the formed battery of tests (606);

c) analyzing (608) responses to the substantially non-validated tests; and d) correlating (610) responses with the responses from the other tests (609) in the formed battery of tests.

Existing data, describing the significance of normal use activities, is, in the main, weak. The simplest advantageous use of normal use activity monitoring is to create advisory notices to the attending professional whenever normal use changes occur. The professional, then, can decide to bring forward further testing.

Alternatively, in the event that there are no changes in monitored normal use, an attending professional, in many circumstances, is likely to approve an occasional postponement of a testing event. Again, this is based on his professional assessment of the client and supplemented by an observation of stability or improvement in a normal use metric.

The introduction of monitoring normal use activities for advancing or postponing testing events will, inevitably, result in accumulation of a large ensemble of data. From this data, monitored normal use can be correlated with validated testing instruments. It is not unlikely to presume that metrics of monitored normal use activities will become valid substitutes for numerous clinical diagnostic testing instruments.

This also supports the objective of the present invention, allowing the professional to manage a large body of clients and reduce the testing burden of clients.

More specifically, results of applied non-validated normal activities tests are compared with results of validated tests. This technique allows for the expansion and validation of normal activities tests. Resulting from this, it becomes possible to use normal activities for providing valid but non-burdensome tests, especially, but not exclusively, for clients where more conventional testing is problematic. Normal activities testing methods become, then, a classical testing instrument.

Figure 7:
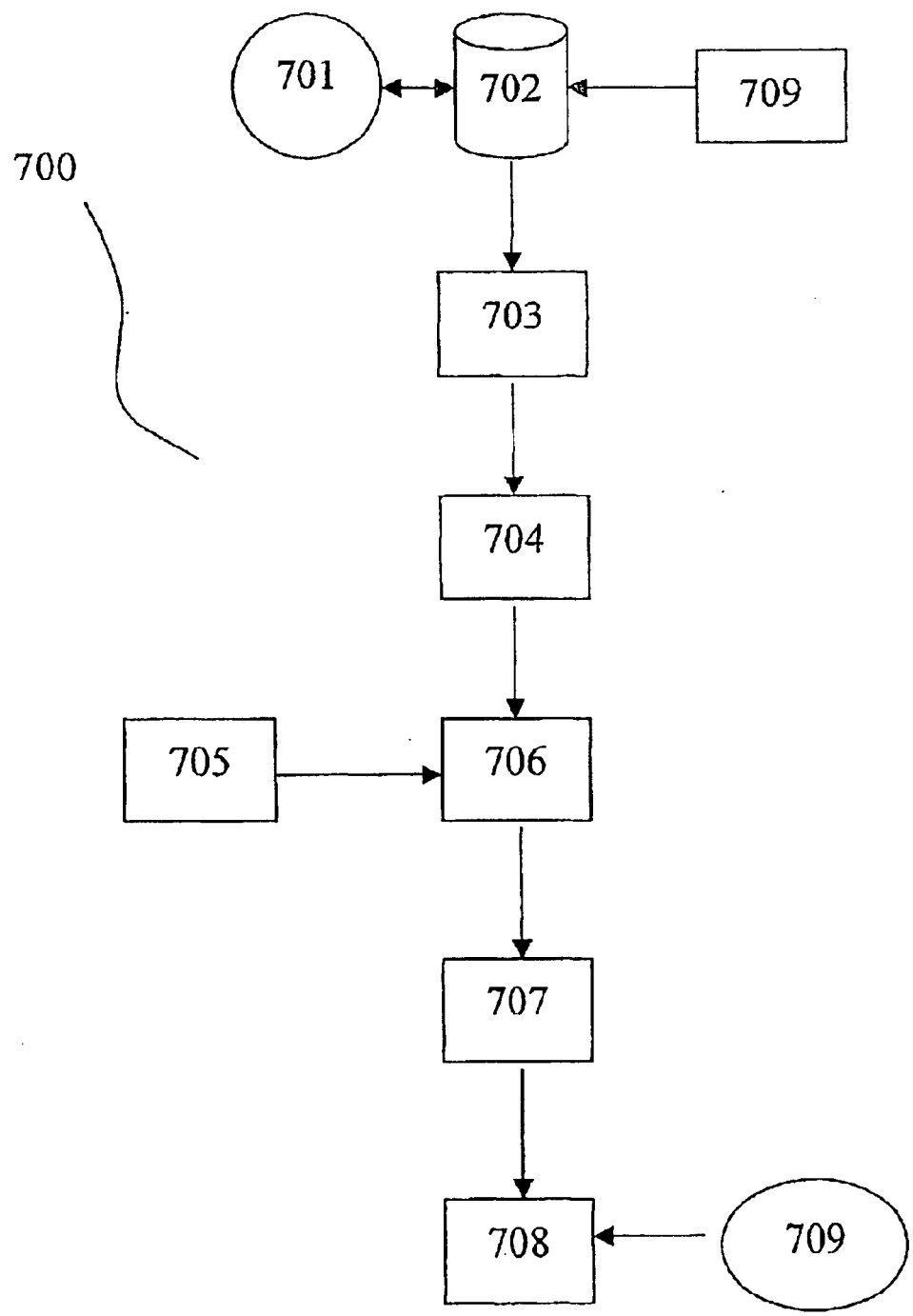
FIG. 7 illustrates a schematic view characterizing the steps of establishing, upgrading and maintaining in the protocol for validating a non-validated test in a formed battery of validated tests by correlating responses from the validated and non-validated tests.

FIG. 7 illustrates a schematic view (700) characterizing the steps indicated in FIG. 6 of establishing (601), upgrading (602) and maintaining (603) in the protocol for validating a non-validated test in a formed battery of validated tests, by correlating responses from the validated and non-validated tests.

According to a variation of embodiments of the present invention, the clinical protocol for normal-use activities, establishing, upgrading and maintaining, include:

a) for substantially each client (701) in an ensemble of clients, monitoring (703) at least one metric of normal-use (702) activities;

b) for substantially each metric of the at least one metric of normal use activities, until a predetermined threshold of validation is achieved for an ensemble of clients, first managing (704) a virtual clinical neuro-psychological testing program for substantially each client in the ensemble; and correlating (706) analytical metrics derived from the neuro-psychological testing program with the monitored metrics of normal-use (705) activities, thereby validating (707) at least one of the monitored metrics of normal-use activities as a neuro-psychological metric; and c) for substantially each validated metric of the at least one metric of normal use activities, second managing (708) a virtual clinical neuro-psychological testing program for at least one client (709) wherein a validated normal-use activity metric (710) is used as a classical testing instrument.

The consequences of using this software are significant for each of the participants. Benefits to neuro-psychologist professionals will include being able to easily bill for services, the ability to better control a much larger client population, and availability of significantly more up-to-date testing materials. Furthermore, it will provide a facile conduit to consult with appropriate specialists, easily enable the professional to manage referrals and to compare his evaluation with an expert system.

Clients, however, will benefit by making payment only for services actually utilized or needed, results of testing will be easily evaluated, a much broader range of testing materials will be available, and access to a wider range of professional services will be feasible. Significantly, the burden in terms of stress and trauma will be much reduced.

For the researcher, there are also significant advantages. These are: access to a large, well managed client population; an environment to introduce weakly validated testing instruments and improve their validation; well-structured pool of background data to correlate results from testing instruments—allowing validation of these instruments at a lower cost; and provide an easy way to market these now validated tests and receive remuneration, for these now validated tests.

Figure 8:
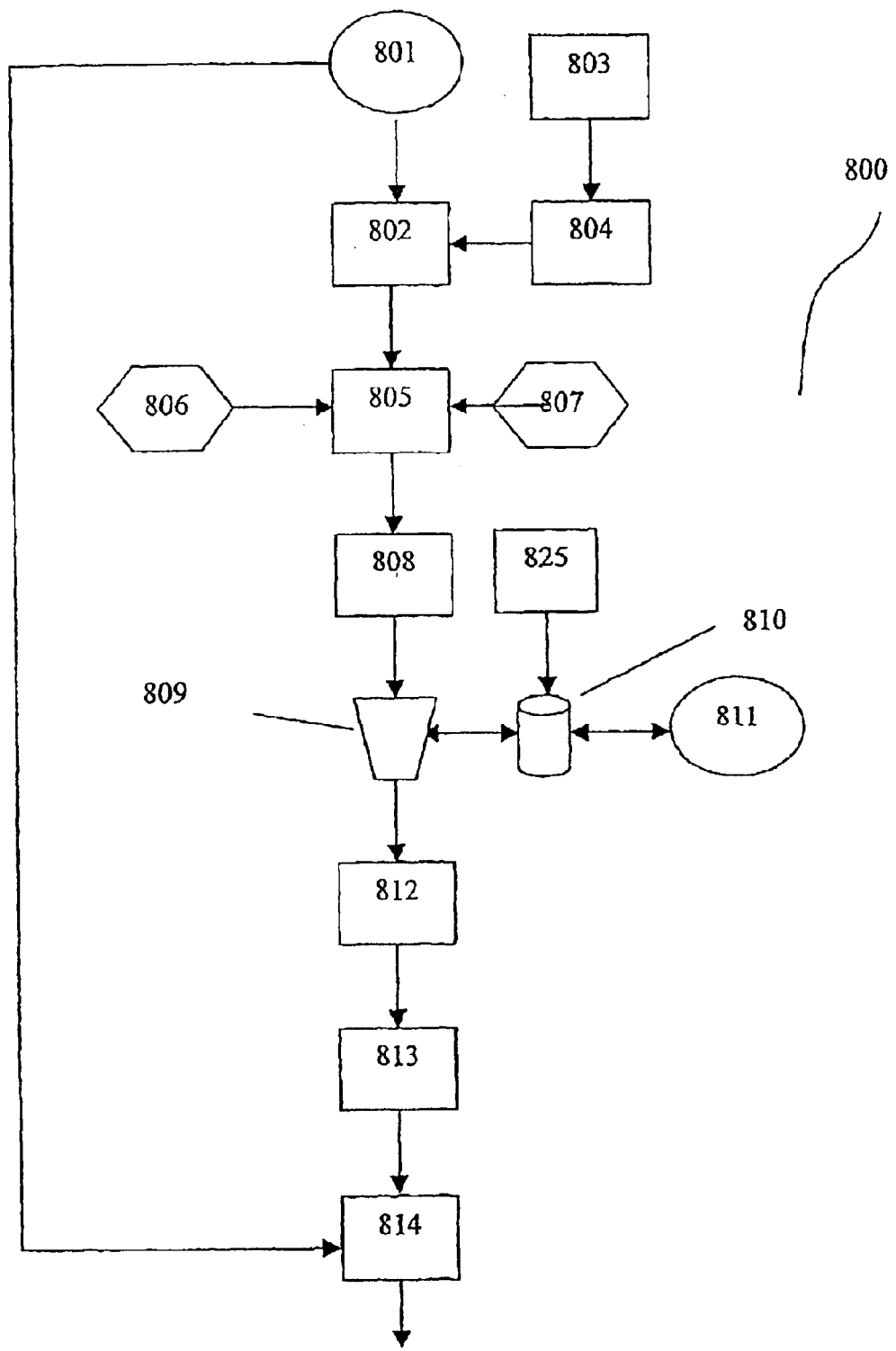
FIG. 8 illustrates a schematic view characterizing the steps of a software driven protocol for managing a virtual clinical neuro-psychological testing program based on normal use activities.

Turning to FIG. 8 which illustrates a schematic view characterizing the steps of a software driven protocol (800) for managing a virtual clinical neuro-psychological testing program based on normal use activities The present invention furthermore relates to a software-driven protocol for managing a virtual clinical neuro-psychological testing program based on normal use activities, the protocol including for each client (801) of a plurality of clients the steps:

a) evaluating (802) of a prior history (804) of the client;

b) according to the evaluated prior history, forming (805) at least one normal use activity factor of tests (806) for testing the client wherein said at least one normal use activity factor incorporates pseudo-randomization (807) of at least one representational or organizational parameter;

c) via a data-communications medium (809), interactively (810)
   i. delivering (808) the formed at least one normal use activity factor tests to the client (811),
   ii. the client substantially completing the normal use activity factor tests, and
   iii. accepting (812), from the client, a substantially completed response to the delivered normal use activity factor tests;

d) analyzing (813) the accepted response; and e) into the prior history (801) of the client, integrating (814)
   i. the accepted substantially completed response or
   ii. at least one analytical metric thereof.

This further apparent repetition of aspects and certain embodiments of the present invention has been necessitated due to additional differences in emphasis. In the particular case that has been dealt with, the emphasis has changed from managing a testing program, from validation of normal activities testing and from managing a virtual clinical neuro-psychological dynamic hierarchical testing program, to managing a virtual clinical neuro-psychological testing program based on normal use activities.

More specifically, there is a presumption that there are validated testing instruments. Nevertheless, substantially every neuro-psychologist of an expert level agrees that there is no substantial substitute for observing the client and interacting with the client until such time as the attending professional is convinced that he has an understanding of inter-related functional aspects of the client's state.

According to any of the embodiments of the present invention, the protocol in which forming an appropriate battery of tests includes choosing in FIG. 1 (106), in FIG. 3 (307), in FIG. 4 (404), in FIG. 5 (506), and in FIG. 8 (806), at least two tests for measuring at least one mental or motor function, and the tests are selected from the list of testing instruments for measuring: mental health, intelligence, IQ, memory, immediate recall, memory encoding, memory retrieval, working memory, semantic memory, procedural learning, sequence learning, conditioned response, Pavlovian learning, associative learning, implicit learning, explicit learning, block learning, motor learning, pattern matching, judgment, attention, concentration, visual-spatial perception, velocity perception, distance perception, visual searching, calculational ability, mathematical ability, abstract thinking, symbolic thinking, adaptation, sensory-motor adaptation, language, reading, naming, comprehension, classification, direction-following, vigilance, motor, sensory-motor, coordination, psychomotor performance, dexterity, motor skills, tremor, physiological tremor, simple reaction time, choice reaction time, sustained attention, selected attention, divided attention, driving safety, ballistic movement, bradykinesia, hypokinesia, akinesia, hypometria, movement speed, movement smoothness, movement accuracy, repetitive movement, accurately timed movements, bimanual coordination, hand-eye coordination, personality, scholastic performance, depression, psychosis, neurosis, anxiety, stress, post-traumatic stress, dementia, static visual acuity, dynamic visual acuity, handwriting analysis, speech analysis, voice tremor, or metrics of interacting with a testing instrument.

According to any of the embodiments of the present invention, the protocol in which forming occurs, includes for at least one test in the battery of tests defining a subset of equivalent validation of testing objects and therein pseudo randomization includes randomizing amongst the substantially validated testing objects.

Simply stated, an additional means of validation of testing may be facilitated in accordance with embodiments to the present invention. By insertion of a number of condition non-specific tests randomly within established and validated tests and batteries of tests, the clinician will be able to accumulate data to validate these inserted tests or sub-tests.

Expanding on the scope and multiplicity of neuro-psychological testing will enable the professional clinician to expand the scope and depth of investigative testing and will improve the ability to manage a substantially larger client base with improved levels of professional service.

According to any of the embodiments of the present invention, the protocol in which evaluating occurs, includes a disclosure of information by the client.

According to any of the embodiments of the present invention the protocol in which evaluating of a prior history of the client occurs, includes: interactively merging (104), (503) or (804), practitioner recommendations (103), (502) or (803), for this client into the prior history.

According to any of the embodiments of the present invention, the protocol further includes the step of scheduling a next evaluating of a prior history of the client.

Notwithstanding the existence or the original or current mode of arranging monitoring of the client, scheduling a next evaluating of a prior history of the client means simply scheduling the next testing selection, or alternatively, scheduling describes bringing scheduling out of automatic mode to the eyes of the expert professional. Even if normal use activity has no validation as a metric, nevertheless, monitored normal use should either cause the next scheduling to be advanced or should cause the professional to re-certify his evaluation.

According to any of the embodiments of the present invention, the protocol in which analyzing the accepted response occurs, includes: calculating (117), an analytical metric of client performance using the accepted response in the formed battery of tests of at least one client performance parameter from the accepted response of a test in the formed battery of tests. This analyzing and calculating, simply stated, means appreciating the significance of the results of a single variable testing instrument According to any of the embodiments of the present invention, the protocol in which analyzing the accepted response occurs, includes: calculating (118), an analytical metric of client performance using the accepted response in the formed battery of tests of at least one convergence parameter from the accepted response of at least two tests in the formed battery of tests.

In this calculating an analytical metric of client performance, neuro-psychological testing makes use of multi-parametric instead of single variable factors. This analyzes and calculates the results of more than one variable converging to a significant definition of the client's condition.

According to any of the embodiments of the present invention, the protocol of a test of the delivered and accepted formed battery of tests includes a metric of the clients interaction with a client's peripheral device, and the device is selected from the list: Color graphic display; B/W graphic display; Audio speaker; Audio stereophonic headphones; Mouse; Joystick; Roller-ball; Keyboard; Galvanic skin response monitor; Web-cam camera; Microphone; personal communication device; Touch pad, Touch screen; etc.

Simply stated, the client's testing will include interaction, from test to test, with a peripheral device, and includes examining such effects as speed of operation, consistency of color discernment, mouse or joystick tremor, speech variations, etc.

According to another embodiment of the present invention, the clinical protocol for substantially each client in an ensemble of clients, monitoring at least one metric of normal-use activities includes downloading a plug-in (205, 207, 209, etc.) and (805) to the client's machine, installing the plug-in, and uploading data collected by the plug-in, etc.

According to an embodiment of the present invention, in the clinical protocol for substantially each client in an ensemble of clients, monitoring at least one metric of device-dependent normal-use activities, includes copying, pasting, editing, inserting, formatting, exchanging tasks, web surfing, keyboard backspacing, deleting and shifting, etc.

More specifically, the application of device dependent testing capable of software enablement as well as various data communication systems is important in the application of normal activities testing techniques, for example:

a) A personal computer, Internet enabled, where measurements are possible, relating to keyboard use, mouse use, etc.

b) Palm-held computer which, on occasion, interacts with various types of data communication devices, can be applied to normal activity testing using the key-pad, using the search and select functions, using stylus and other data entering modes, etc.

c) Personal communication devices such as cellular telephones are also applicable.

Making use of functions including key-pad use, device function uses like dialing or searching, voice print access interpreting the level of various actions like slurring or decipherability, etc. are significant measures.

According to a subsequent embodiment of the present invention, in the clinical protocol for substantially each client in an ensemble of clients, monitoring at least one metric of normal-use activities, includes computer related interactivity, wireless activity, voice prints frequency analysis, mouse tremor, Geographic Positioning System tremor, key strokes, and special case use, etc.

Simply put, monitoring normal use activities such as those listed, enables the neuro-psychological professional to make decisions regarding the state of a client, whether such testing has been validated or not. Significance can even be placed on monitoring unvalidated tests simply by making comparisons over a period of time. Properly validated tests will give considerably more information to a clinician. Changes in a monitored factor would indicate to the professional, that a client requires further testing immediately or at some later time. Monitoring of these factors can be on a continuous basis or simply whenever the client makes use of any of the data communication devices available.

A direct consequence to use of this software and plug-ins is:

a) maintaining and improving professional neuro psychologists' ability to manage large client bases with an appropriate level of professional service, b) billing control for testing becomes a straightforward matter for both client and clinician, c) cost of testing will be substantially reduced, d) time demands and requirements will be substantially reduced e) providing clients with equal or lower test participation and simpler active cooperation with test instruments, f) the possibility of constant online contact and interaction between client and clinician, and g) reduced testing burden for the client.

Figure 10:
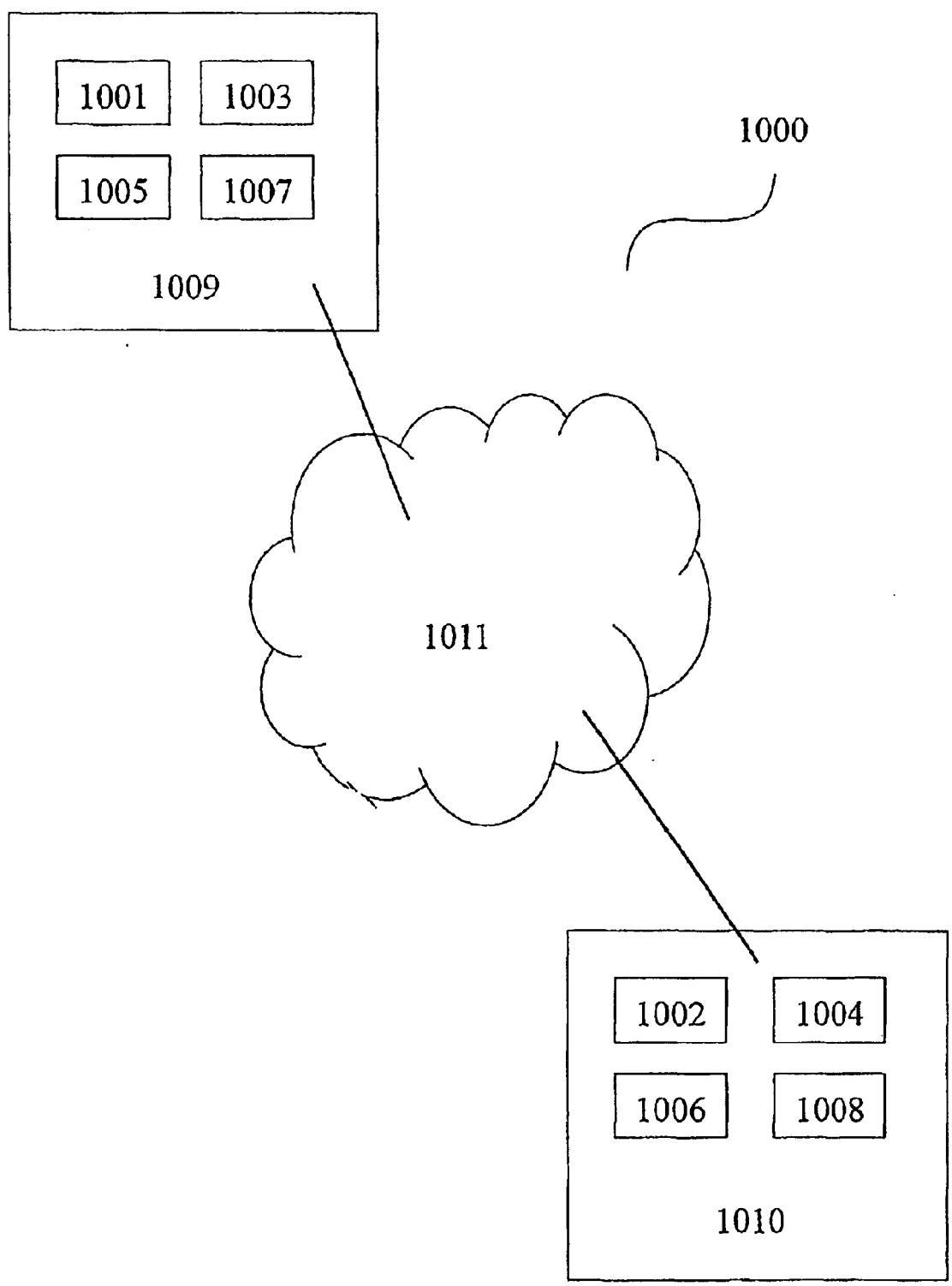
FIG. 10 illustrates a schematic view characterizing the steps of a computer program product including a computer usable medium having computer readable code embodied therein for a software driven protocol for managing a virtual clinical neuro-psychological testing program.

FIG. 10 illustrates a schematic view characterizing the steps of a computer program product (1000) including a computer usable medium having computer readable code (1011) embodied therein for a software driven protocol for managing a virtual clinical neuro psychological testing program.

The present invention additionally relates to a computer program product (1000) including a computer usable medium having computer readable program code embodied therein for a software-driven protocol (1001) for managing a virtual clinical neuro-psychological testing program, on the clinician side (1009), the computer readable program code in said article of manufacture including: for each client of a plurality of clients:

a) first computer readable program code for causing a computer to evaluate a prior history of the client;

b) tied to the first computer readable code, second computer readable program code for causing the computer, according to the evaluated prior history, to form an appropriate battery of tests for testing the client wherein said battery incorporates pseudo-randomization of at least one representational or organizational parameter;

c) tied to second computer readable code, third computer readable program code for causing the computer, via a data-communications medium, to interactively deliver to the client the formed battery of tests, and to accept from the client a substantially completed response to the delivered formed battery of tests;

d) tied to third computer readable program code, fourth computer readable program code for causing the computer to analyze the accepted response; and e) tied to the fourth computer readable program code, fifth computer readable program code for causing the computer, into the prior history of the client to, integrate the accepted substantially completed response or at least one analytical metric thereof The present invention collaterally relates to a computer program product including a computer usable medium having computer readable program code embodied therein for, a client side (1010) compliance with a software-driven protocol (1002) for managing a virtual clinical neuro-psychological testing program, the computer readable program code in said article of manufacture including:

a) first computer readable program code for causing the computer to, via a data-communications medium, interactively, receive by the client, the formed battery of tests;

b) the client to substantially complete the tests; and c) the client to return the substantially completed response to the formed battery of tests.

The present invention likewise relates to a computer program product including a computer usable medium having computer readable program code embodied therein for, clinician side (1009) management of a clinical protocol (1003) for normal-use activities, the computer readable program code in said article of manufacture including:

a) first computer readable program code for causing the computer, for substantially each client in an ensemble of clients, to monitor at least one metric of normal-use activities;

b) tied to the first computer readable program code, second computer readable program code for causing the computer, for substantially each metric of the at least one metric of normal use activities, until a predetermined threshold of validation is achieved for an ensemble of clients, to first manage a virtual clinical neuro-psychological testing program for substantially each client in the ensemble; and to correlate analytical metrics derived from the neuro-psychological testing program with the monitored metrics of normal-use activities, thereby to validate at least one of the monitored metrics of normal-use activities as a neuro-psychological metric; and c) tied to the second computer readable program code, third computer readable program code for causing the computer, for substantially each validated metric of the at least one metric of normal use activities, to second manage a virtual clinical neuro-psychological testing program for at least one client wherein a validated normal-use activity metric is used as a classical testing instrument.

The present invention further relates to a computer program product including a computer usable medium having computer readable program code embodied therein, on the client side (1010), for a clinical protocol (1004) for normal-use activities, the computer readable program code in said article of manufacture including:

a) first computer readable program code for causing the computer, for substantially each client in an ensemble of clients, to monitor at least one metric of normal-use activities by the client;

b) tied to the first computer readable program code, second computer readable program code for causing the computer, for substantially each validated metric of the at least one metric of normal use activities, for at least one client to perform a virtual clinical neuro-psychological testing program wherein a validated normal-use activity metric is used as a classical testing instrument.

The present invention also relates to a computer program product including a computer usable medium having computer readable program code embodied therein for a software-driven protocol (1005) for the managing a virtual clinical neuro-psychological dynamic hierarchical testing program, on the clinician side (1009), the computer readable program code in said article of manufacture including for each client of a plurality of clients:

a) first computer readable program code for causing a computer to evaluate a prior history of the client;

b) tied to the first computer readable program code, second computer readable program code for causing the computer, according to the evaluated prior history, to:

i. interactively form an appropriate battery of tests for testing the client wherein said battery incorporates pseudo-randomization of at least one representational or organizational parameter;

ii. via a data-communications medium, interactively deliver to the client the formed battery of tests, iii. accept from the client a substantially completed response to the delivered formed battery of tests;

iv. analyze the accepted response; and v. return to step b)i until complete; and c) tied to the second computer readable program code, third computer readable program code for causing the computer, into the prior history of the client, to integrate:

i. the accepted substantially completed response or ii. at least one analytical metric thereof.

The present invention furthermore relates to a computer program product including a computer usable medium having computer readable program code embodied therein for, a client side (1010) compliance with a software-driven protocol (1006) for managing a virtual clinical neuro-psychological dynamic hierarchical testing program, the computer readable program code in said article of manufacture, tied to the first computer readable program code, second computer readable program code for causing the computer, according to the evaluated prior history:

a) via a data-communications medium, the client, interactively to receive the test program, b) the client to substantially complete a response to the delivered test program, and c) via a data-communications medium, the client to return the substantially complete test program.

The present invention likewise, relates to a computer program product including a computer usable medium having computer readable program code embodied therein for a software-driven protocol (1007) for managing a virtual clinical neuro-psychological testing program based on normal use activities, on the clinician side (1009), the protocol, for each client of a plurality of clients, the computer readable program code in said article of manufacture including;

a) first computer readable program code for causing a computer to evaluate a prior history of the client;

b) tied to the first computer readable code, second computer readable program code for causing the computer to, according to the evaluated prior history, form at least one normal use activity factor of tests for testing the client wherein said at least one normal use activity factor incorporates pseudo-randomization of at least one representational or organizational parameter;

c) tied to the second computer readable code, third computer readable program code for causing the computer, via a data-communications medium, to interactively
 i. deliver the formed at least one normal use activity factor tests to the client,
 ii. the client substantially complete the normal use activity factor tests, and
 iii. accept, from the client, a substantially completed response to the delivered normal use activity factor tests;

d) analyze the accepted response; and
e) integrate into the prior history of the client.

The present invention similarly relates to a computer program product including a computer usable medium having computer readable program code embodied therein for a software-driven protocol (1008) for managing a virtual clinical neuro-psychological testing program based on normal use activities, on the client side (1010), the protocol, for each client of a plurality of clients, the computer readable program code in said article of manufacture including:

a) first computer readable program code for causing the computer, via a data-communications medium, to interactively
 i. receive the formed at least one normal use activity factor tests by the client,
 ii. the client substantially complete the normal use activity factor tests, and
 iii. send from the client, the substantially completed response to the delivered normal use activity factor tests.

Figure 11:
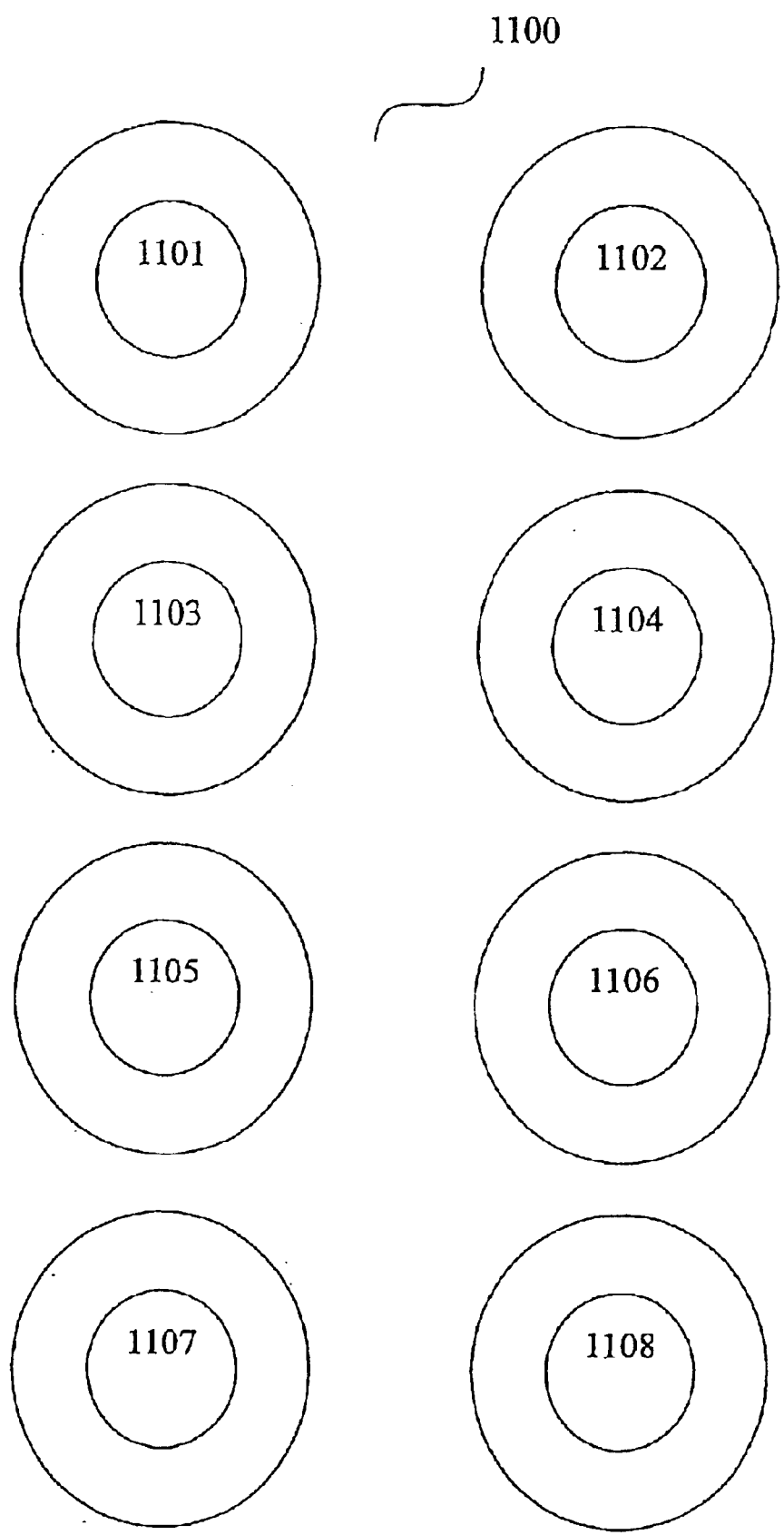
FIG. 11 illustrates a schematic view characterizing a program storage device readable by machine, tangibly embodying a program of instructions executable by the machine to perform method steps for a software driven protocol for managing a software driven protocol for managing a virtual clinical neuro-psychological testing program.

FIG. 11 illustrates a schematic view characterizing a program storage device (1100) readable by machine, tangibly embodying a program of instructions executable by the machine to perform method steps for a software driven protocol for managing a software driven protocol for managing a virtual clinical neuro psychological testing program.

The present invention, in addition, relates to a program storage device readable by machine, tangibly embodying a program of instructions executable by the machine to perform method steps for a software-driven protocol (1101) for managing a virtual clinical neuro-psychological testing program, the protocol including for each client of a plurality of clients, on the clinician side, steps including:

a) evaluating of a prior history of the client;
b) according to the evaluated prior history, forming an appropriate battery of tests for testing the client wherein said battery incorporates pseudo-randomization of at least one representational or organizational parameter;
c) via a data-communications medium, interactively
 i. delivering, to the client, the formed battery of tests, and
 ii. accepting, from the client, a substantially completed response to the delivered formed battery of tests;
d) analyzing the accepted response; and
e) into the prior history of the client, integrating
 i. the accepted substantially completed response or
 ii. at least one analytical metric thereof.

The present invention additionally relates to a program storage device readable by machine, tangibly embodying a program of instructions executable by the machine to perform method steps for a software-driven protocol (1102) for managing a virtual clinical neuro-psychological testing program, the protocol including for each client of a plurality of clients, on the client side, steps including:

a) via a data-communications medium, interactively the client receiving the formed battery of tests,
b) the client substantially completing the formed battery of tests, and
c) via a data-communications medium, the client sending, a substantially completed response to the delivered formed battery of tests.

The present invention in addition relates to a program storage device readable by machine, tangibly embodying a program of instructions executable by the machine to perform method steps for, in the clinician side, a clinical protocol (1103) for normal-use activities, steps including:

a) for substantially each client in an ensemble of clients, monitoring at least one metric of normal-use activities;
b) for substantially each metric of the at least one metric of normal use activities, until a predetermined threshold of validation is achieved for an ensemble of clients, first managing a virtual clinical neuro-psychological testing program for substantially each client in the ensemble; and correlating analytical metrics derived from the neuro-psychological testing program with the monitored metrics of normal-use activities, thereby validating at least one of the monitored metrics of normal-use activities as a neuro-psychological metric; and
c) for substantially each validated metric of the at least one metric of normal use activities, second managing a virtual clinical neuro-psychological testing program for at least one client wherein a validated normal-use activity metric is used as a classical testing instrument.

The present invention additionally relates to a program storage device readable by machine, tangibly embodying a program of instructions executable by the machine to perform method steps for, in the client side, a clinical protocol (1104) for normal-use activities, said method steps including:

a) for substantially each client in an ensemble of clients, performing at least one metric of normal-use activities;
b) for substantially each metric of the at least one metric of normal use activities, until a predetermined threshold of validation is achieved for an ensemble of clients, carrying out a virtual clinical neuro-psychological testing program by substantially each client in the ensemble; and
c) for substantially each validated metric of the at least one metric of normal use activities, carrying out a virtual clinical neuro-psychological testing program wherein a validated normal-use activity metric is used as a classical testing instrument.

Further, the present invention also relates to a program storage device readable by machine, tangibly embodying a program of instructions executable by the machine to perform method steps for, on the clinician side, a software-driven protocol (1105) for managing a virtual clinical neuro-psychological dynamic hierarchical testing program, the protocol including for each client of a plurality of clients the steps:

a) evaluating of a prior history of the client;
b) according to the evaluated prior history,
 i. interactively forming an appropriate battery of tests for testing the client wherein said battery incorporates pseudo-randomization of at least one representational or organizational parameter;
  ii. via a data-communications medium, interactively delivering, to the client, the formed battery of tests,
  iii. accepting, from the client, a substantially completed response to the delivered formed battery of tests;
  iv. analyzing the accepted response; and
  v. returning to step b)i until complete; and
c) into the prior history of the client, integrating
  i. the accepted substantially completed response or
  ii. at least one analytical metric thereof.

Moreover the present invention also relates to a program storage device readable by machine, tangibly embodying a program of instructions executable by the machine to perform method steps for, on the client side, a software-driven protocol (1106) for managing a virtual clinical neuro-psychological dynamic hierarchical testing program, the protocol said method including for each client of a plurality of clients the steps:
a) via a data-communications medium, interactively the client receiving, from the clinician, the formed, dynamic hierarchical testing program;
b) the client substantially carrying out the received tests,
c) via a data-communications medium, the client sending, a substantially completed response to the delivered tests.

In addition the present invention likewise relates to a program storage device readable by machine, tangibly embodying a program of instructions executable by the machine to perform method steps for, a software-driven protocol (1107) for managing a virtual clinical neuro-psychological testing program based on normal use activities, the protocol including, on the clinician side, for each client of a plurality of clients the said method steps including:
a) evaluating of a prior history of the client;
b) according to the evaluated prior history, forming at least one normal use activity factor of tests for testing the client wherein said at least one normal use activity factor incorporates pseudo-randomization of at least one representational or organizational parameter;
c) via a data-communications medium, interactively
  i. delivering the formed at least one normal use activity factor tests to the client,
  ii. the client substantially completing the normal use activity factor tests, and
  iii. accepting, from the client, a substantially completed response to the delivered normal use activity factor tests;
d) analyzing the accepted response; and
e) into the prior history of the client, integrating
  i. the accepted substantially completed response or
  ii. at least one analytical metric thereof.

Finally, the present invention also relates to a program storage device readable by machine, tangibly embodying a program of instructions executable by the machine to perform method steps for, a software-driven protocol (1108) for managing a virtual clinical neuro-psychological testing program based on normal use activities, the protocol including, on the client side, for each client of a plurality of clients the said method steps including:
a) via a data-communications medium, the client, interactively receiving the formed at least one normal use activity factor tests;
b) the client substantially completing the normal use activity factor tests, and
c) via a data-communications medium, the client returning a substantially completed response to the delivered normal use activity factor tests.

Having described various large-scale embodiments of the present invention, it would seem appropriate to introduce some of the novel working components, which are incorporated into the various embodiments.

At present, in the field of neuro-psychology, a trained, fully qualified expert should have the opportunity to spend a substantial amount of time with each client. This time should include a significant amount of observation and testing, on and one-on-one basis. Unfortunately, a shortage of fully trained, expert, professionals in this field, has given rise to relatively few clients receiving sufficient testing and adequate treatment. The present invention seeks to address this problem.

It should be understood, at the outset, that a neuro psychologist professional has, as a prime objective, a desire to perform as little testing as possible on each client, to spare clients from some of the inevitable stress and trauma resulting from any testing. Furthermore, if such testing can be largely limited to normal activity testing, this would present each client with a minimum of stress and trauma.

Registering a new client: For the facile convenience of the attending clinician, a template is provided when registering a new client (and, optionally, when a clinician intervenes by evaluating that client's performance). The template targets potential functions that may be important in an evaluation of the following situations:

1. Normal life activity including aging—even in people who are not thought to have a disease. For example, measuring memory-loss, personality change, confusion, delirium, slowed motor function, decreased dexterity, poor coordination, tremor, driving safety, baseline intelligence, baseline personality profile, etc.

2. High level function. For example, vocational evaluation, security clearance, etc. Child developmental metrics. For example, language or speech problems, dyslexia, social problems, behavioral problems, attention deficit hyperactivity disorder (ADHD), poor scholastic performance, hyperactivity, poor attention, motor delay, lack of or poor coordination, mental retardation, intellectual impairment, recommendation for medication, special education, speech therapy, occupational therapy, etc.

3. Dementia (decreased functioning associated with mental decline). For example, to provide information useful for diagnosis and follow-up of Alzheimer's disease or other dementia disorders (such as vascular dementia, dementia caused by depression, AIDS, HIV, and other known causes); decision to initiate medical treatment; decision to change or terminate medical treatment; determine cognitive or motor side effects of drugs; recommendation to stop driving; recommendation for living assistance at home or in an institution; cognitive rehabilitation therapy; standardized tool to judge efficacy and safety of new or existing drugs, etc.

4. Parkinsonian syndromes. For example, to provide information useful for diagnosis and follow-up of Parkinson's disease, and other conditions that result in slowed movement (multiple system atrophy, striatonigral degeneration, diffuse Lewy body disease, progressive supranuclear palsy, frontal lobe syndromes, and other known causes); decision to initiate medical treatment; decision to change or terminate medical treatment; determination of cognitive or motor side effects of drugs; recommendation to stop driving; recommendation for living assistance at home or in institution; cognitive, physical, speech, and occupational rehabilitation therapy; standardized tool to judge efficacy and safety of new or existing drugs. For surgical candidates, to evaluate exclusion factors that would indicate that there is excessive risk to the patient; to evaluate effects of the surgery; to provide objective information to guide adjustment of post-surgical medical or deep brain stimulation therapy (or other therapy, such as adjustment of flow rate from an implanted pump that may deliver medication at pre-programmed rates); etc.

5. Rehabilitation. For example, to evaluate current status and past trends in cognitive and motor function, as it impinges on ADLs; to design focused treatment programs; to evaluate efficacy of treatment and to decide future treatment; to use (versions of) computerized exercises as treatment modalities, etc.

6. Involuntary movements. For example, to characterize and help diagnose uncontrolled movement such as rest tremor, postural tremor, physiological tremor, chorea, ballismus, athetosis, tics, dystonia, myoclonus, dysmetria, action tremor, and cerebellar tremor; to evaluate efficacy of treatment and decide regarding future treatment; etc.

7. Stroke. For example, to evaluate effects of a stroke and to track rehabilitation; to evaluate efficacy of treatment and decide regarding future treatment; determine cognitive or motor side effects of drugs; recommendation to stop driving; recommendation for living assistance at home or in institution; cognitive, physical, speech, and occupational rehabilitation therapy; standardized tool to judge efficacy and safety of new or existing drugs, etc.

8. Epilepsy. For example, to evaluate cognitive and motor status; to evaluate efficacy of treatment and decide regarding future treatment; determine cognitive or motor side effects of drugs; recommendation for living assistance at home or in institution; cognitive, physical, speech, and occupational rehabilitation therapy; standardized tool to judge efficacy and safety of new or existing drugs. For surgical candidates, to evaluate exclusion factors that would indicate that there is excessive risk to the patient; to evaluate effects of the surgery; to provide objective information to guide adjustment of post-surgical medical or deep brain stimulation therapy (or other therapy, such as adjustment of flow rate from an implanted pump that may deliver medication at pre-programmed rates); etc.

9. Multiple sclerosis. For example, to evaluate cognitive and motor status; to evaluate efficacy of treatment and decide regarding future treatment; determine cognitive or motor side effects of drugs; recommendation for living assistance at home or in institution; cognitive, physical, speech, and occupational rehabilitation therapy; standardized tool to judge efficacy and safety of new or existing drugs; etc.

10. Head trauma. For example, to evaluate cognitive and motor status; to evaluate efficacy of treatment and decide regarding future treatment; determine cognitive or motor side effects of drugs; recommendation for living assistance at home or in an institution; cognitive, physical, speech, and occupational rehabilitation therapy; standardized tool to judge efficacy and safety of new or existing drugs; etc.

11. Neuro-toxicology. For example, evaluate effects of chronic alcohol intake; evaluate effects of acute alcohol intoxication; evaluate effects of illicit drugs; evaluate effects of legal sedative drugs (Valium, etc.); evaluate effects of detoxification programs; recommendation for cognitive, physical or occupational therapy; recommendation to stop driving; etc.

12. Psychiatric diseases (depression, mania, psychosis, anxiety, obsessive-compulsive disorder, etc). For example, to evaluate cognitive and motor status; to evaluate efficacy of treatment and decide regarding future treatment; determine cognitive or motor side effects of drugs; recommendation for living assistance at home or in institution; cognitive, physical, speech, and occupational rehabilitation therapy; standardized tool to judge efficacy and safety of new or existing drugs; to evaluate psychiatric comorbidity (conditions present in addition to other neurological or psychiatric disease); etc.

13. Conversion disorders and malingering. For example, used as objective measure to aid in the diagnosis of non-organic neurological syndrome; performance is inconsistent with complaints; detect malingering by negative response bias.

14. Driving ability. For example, on-road testing to determine whether the subject is 'driving while intoxicated'; testing before dispatch; etc.

15. Self-improvement. For example, used by client (with or without clinician recommendation) for practice to improve certain mental or motor skill; the same or similar tests (with parameter randomization) to be used to assess progress of improved performance; etc.

Figure 12:
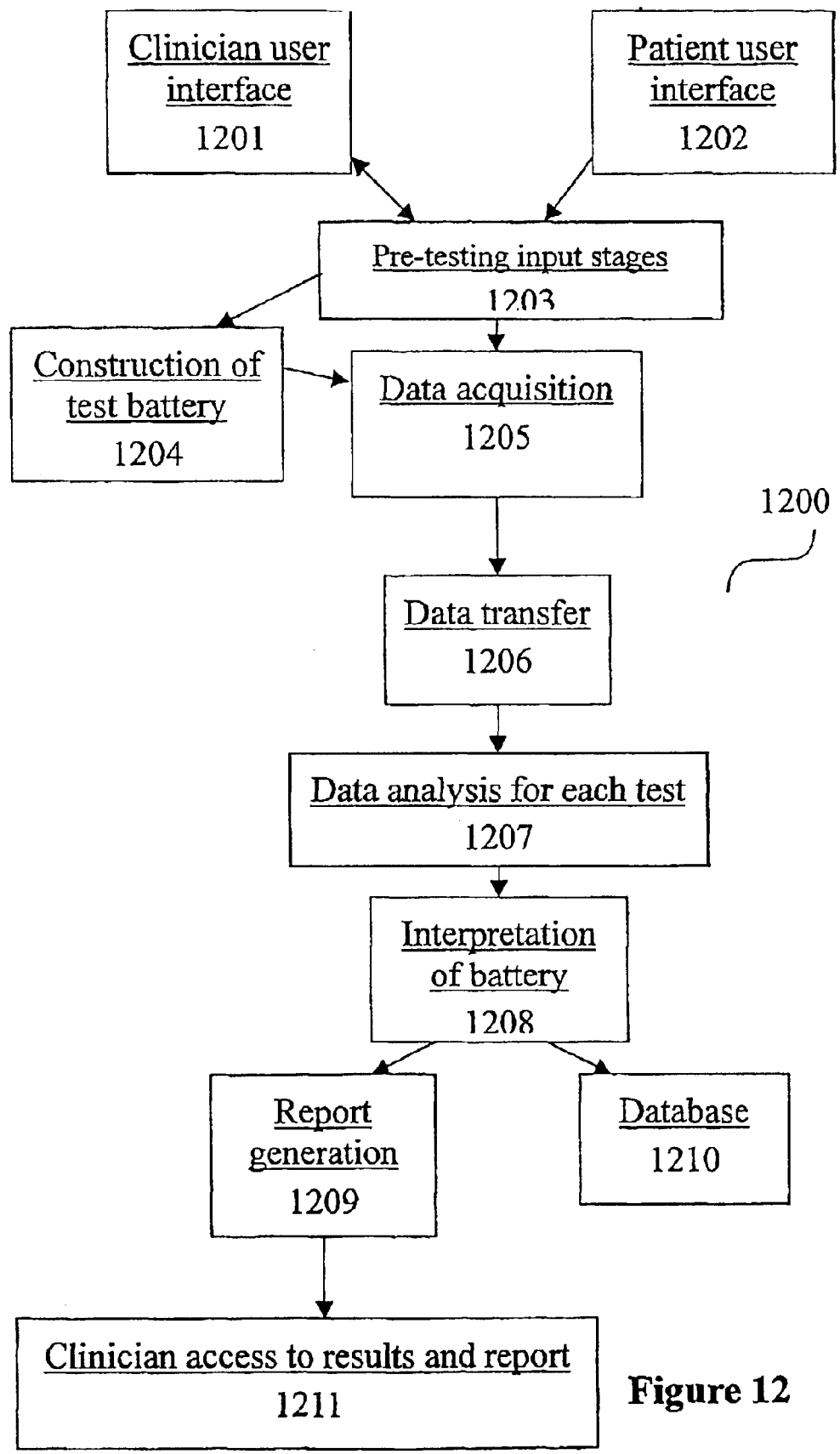
FIG. 12 illustrates a schematic view characterizing a system overview of a software driven protocol for managing a virtual clinical neuro-psychological testing program.

Turning to FIG. 12 which illustrates a schematic view characterizing a system overview (1200) of a software driven protocol for managing a virtual clinical neuro psychological testing program. This system overview includes a number of steps, namely: Clinician user interface (1201), patient user interface (1202), pretesting input stages (1203), construction of test battery (1204), data acquisition (1205), data transfer (1206), data analysis for each test (1207), interpretation of battery (1208), database (1210), report generation (1209) and clinician access to results and report (1211).

Figure 13:
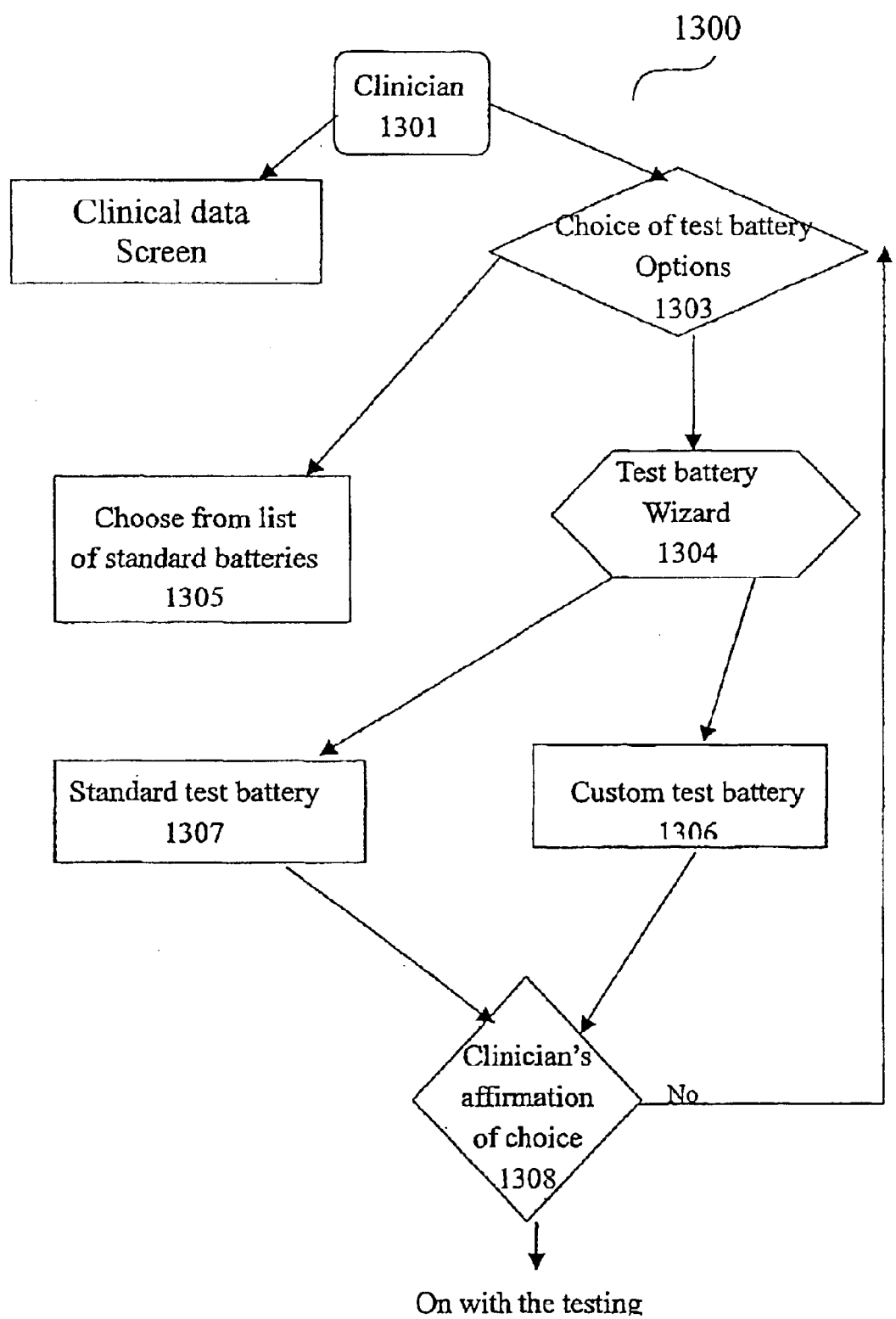
FIG. 13 illustrates a schematic view characterizing the steps of the choice of a test battery for pre-testing in accordance with the software driven protocol for managing a virtual clinical neuro-psychological testing program.

The clinician user interface (1201) procedure is further described in FIG. 13 with regard to pretesting and the choice of a test battery (1300) indicating the clinician (1301) initiating a clinical data screen (1302), choice of test battery options (1303), choosing from a list of standard batteries (1305), utilizing the test battery wizard (1304) with regard to both a custom (1306) and a standard test battery (1307) resulting in the clinician's affirmation of choice (1308) to carry on the testing or to reconsider the choice of test battery options.

Figure 14:
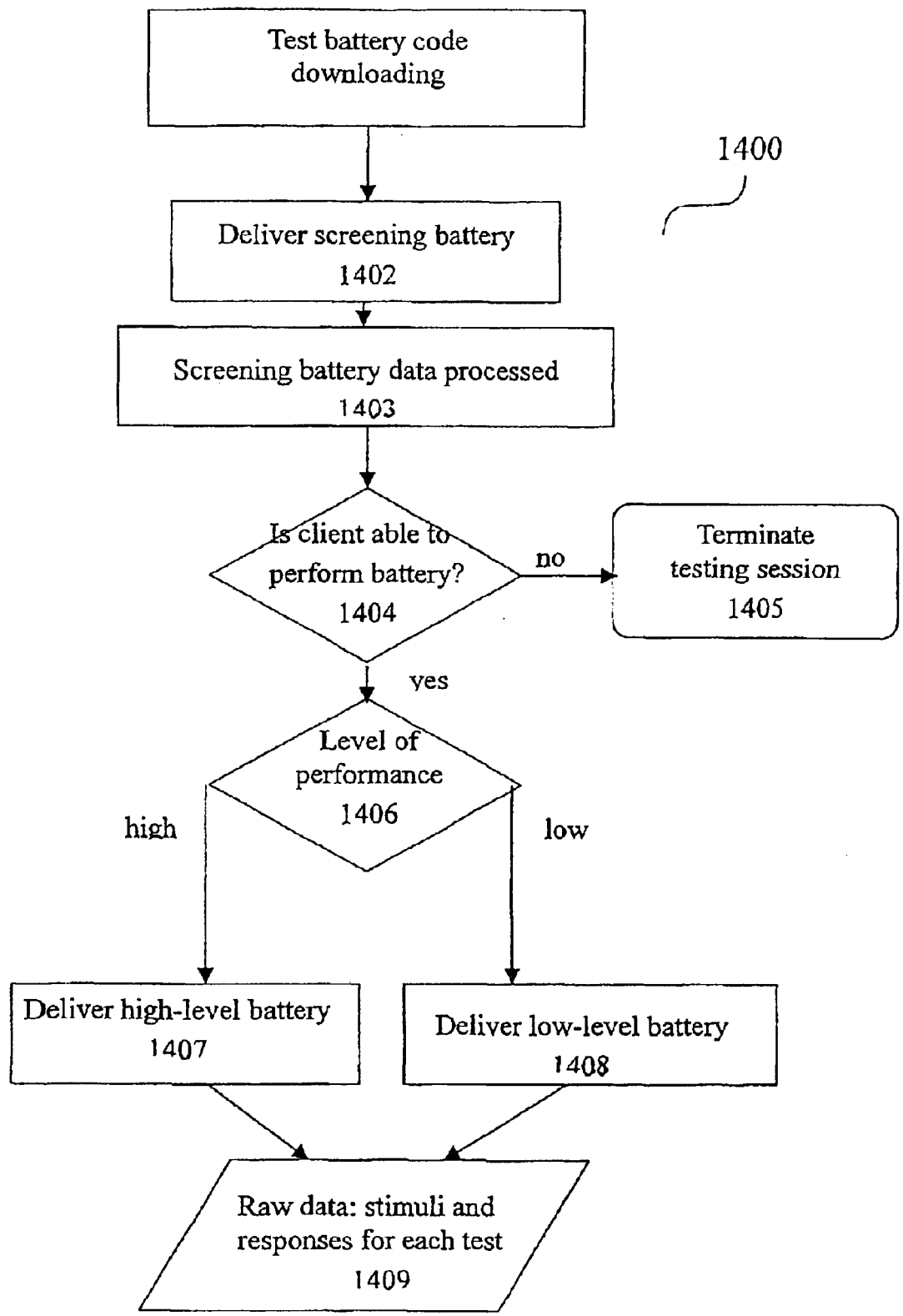
FIG. 14 illustrates a schematic view characterizing the steps of data acquisition in accordance with the software driven protocol for managing a virtual clinical neuro-psychological testing program.

In FIG. 14, the stage of data acquisition (1205) described above, is further expanded (1400) as including the steps of test battery code downloading (1401), delivering screening battery (1402), screening battery data processing (1403), decision (1404) as to whether client is able to perform the battery and, if not, to terminate testing session (1405). If the client is able to perform the battery, the level of performance (1406) is assessed as at a high or at a low level, respectively then resulting in delivery of a high-level (1407) or low-level (1408) battery and this leads to the raw data (1409) stimuli and responses for each test.

Figure 15:
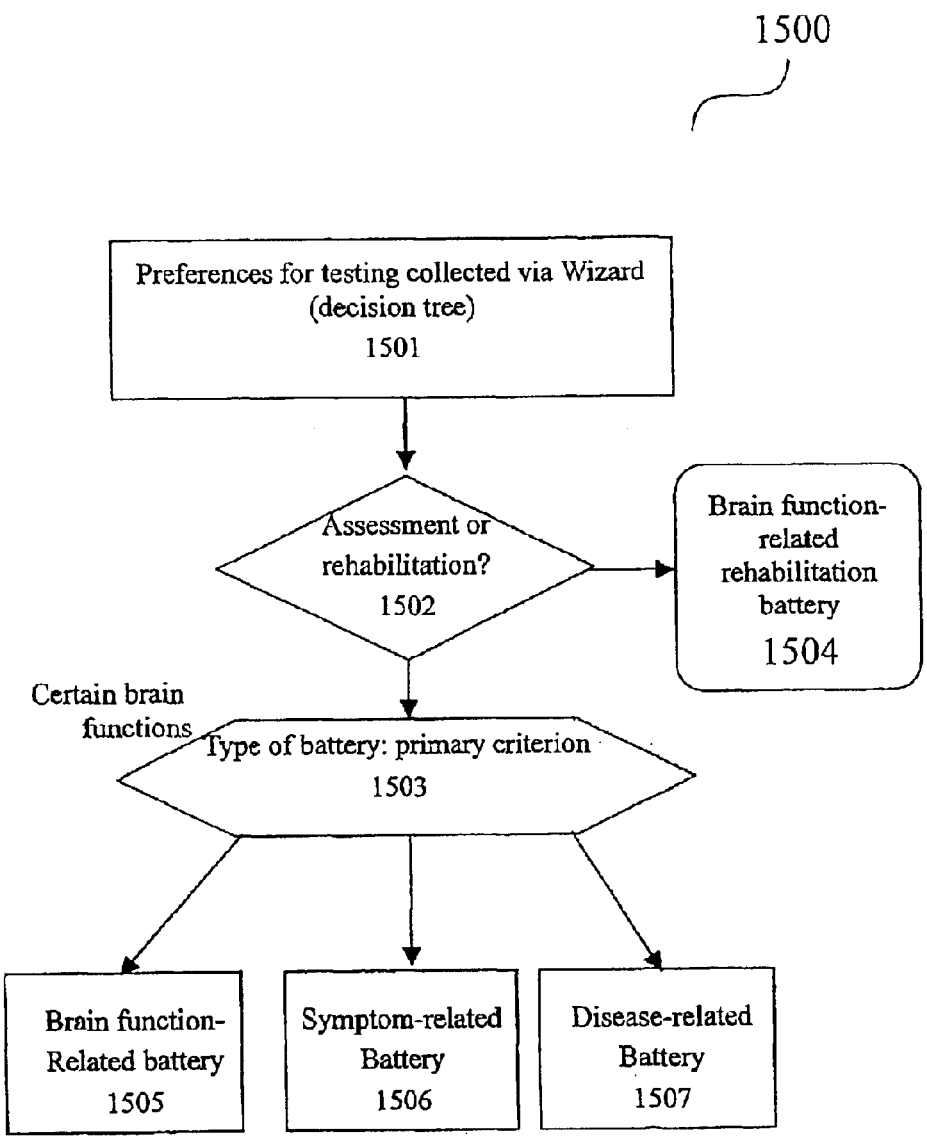
FIG. 15 illustrates a schematic view characterizing the steps of a Test Battery Wizard for use in discerning the nature of a battery of tests required with regard to a client's needs.

FIG. 15 illustrates a schematic view characterizing the steps of a Test Battery Wizard (1500) for use in discerning the nature of a battery of tests required with regard to a client's needs as defined (1200), regarding construction of a test battery (1204). The steps as indicated (1500) are initiated by preferences for testing collected via the wizard (decision tree) (1501), and followed by determining (1502) if there is a need for assessment or rehabilitation. If rehabilitation is indicated, then a brain function related rehabilitation battery (1504) is selected. For further assessment testing, a primary criterion is decided (1503) for the type of battery, namely, brain function related battery (1505), system related battery (1506) or disease related battery (1507).

Figure 16:
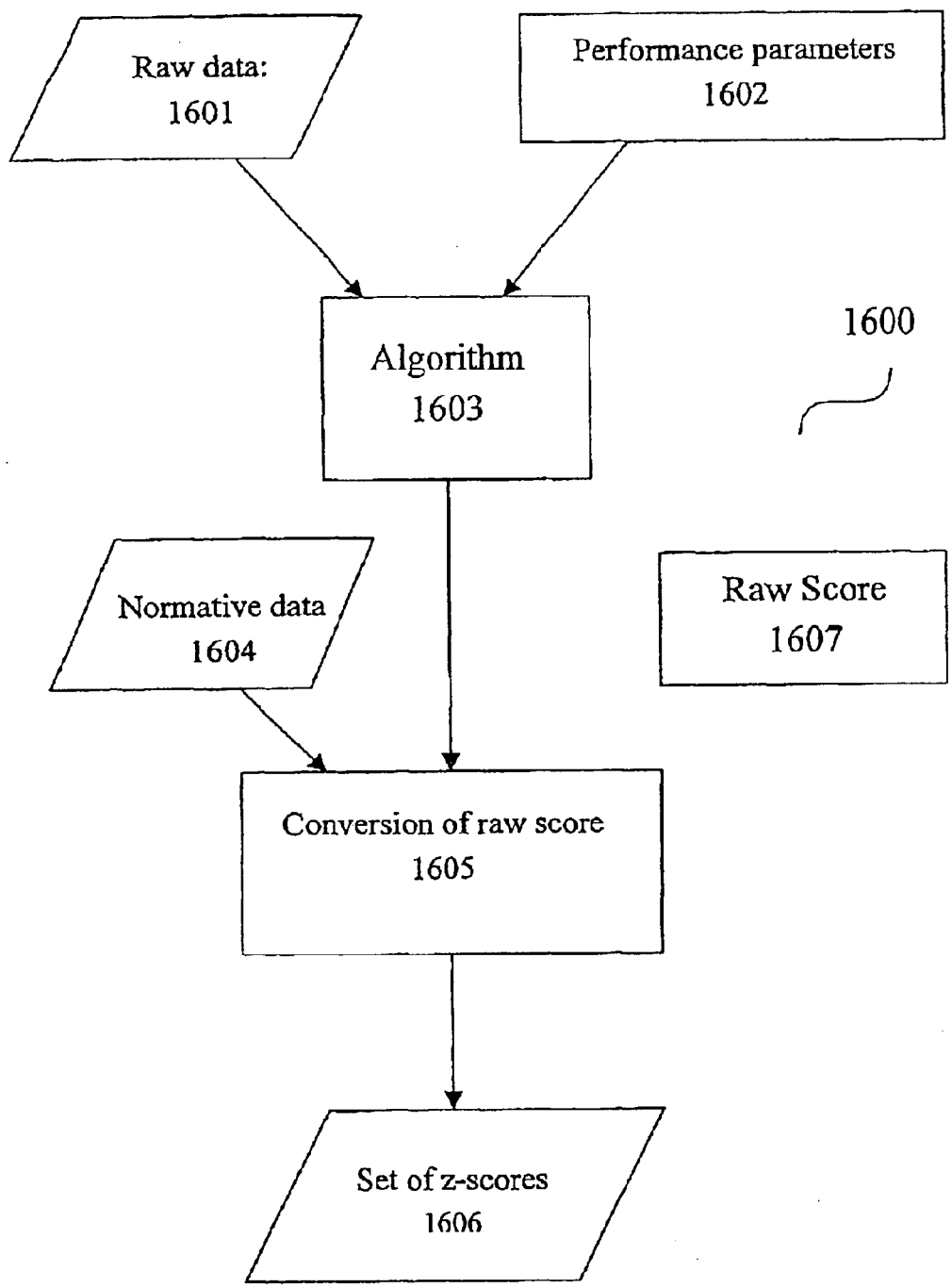
FIG. 16 illustrates a schematic view characterizing the steps of data analysis for each test carried out in accordance with the software driven protocol for managing a virtual clinical neuro-psychological testing program.

Also indicated is the stage (1207) of data analysis for each test further expanded and described in FIG. 16 which illustrates a schematic view characterizing the steps of data analysis (1600) for each test carried out in accordance with the software driven protocol for managing a virtual clinical neuro psychological testing program. These steps include commencing with raw data stimuli and responses (1601) and a set of performance parameters (1602) per design of each test and continues with an algorithm step (1603) for data or signal processing to extract performance parameters (specific for each test) leading to the step (1605) of conversion of raw score to a statistical measure "z-score" for each output parameter when compared with normative data (1604) from the data base, and resulting in set of z-scores (1606) for the entire test battery.

Figure 17:
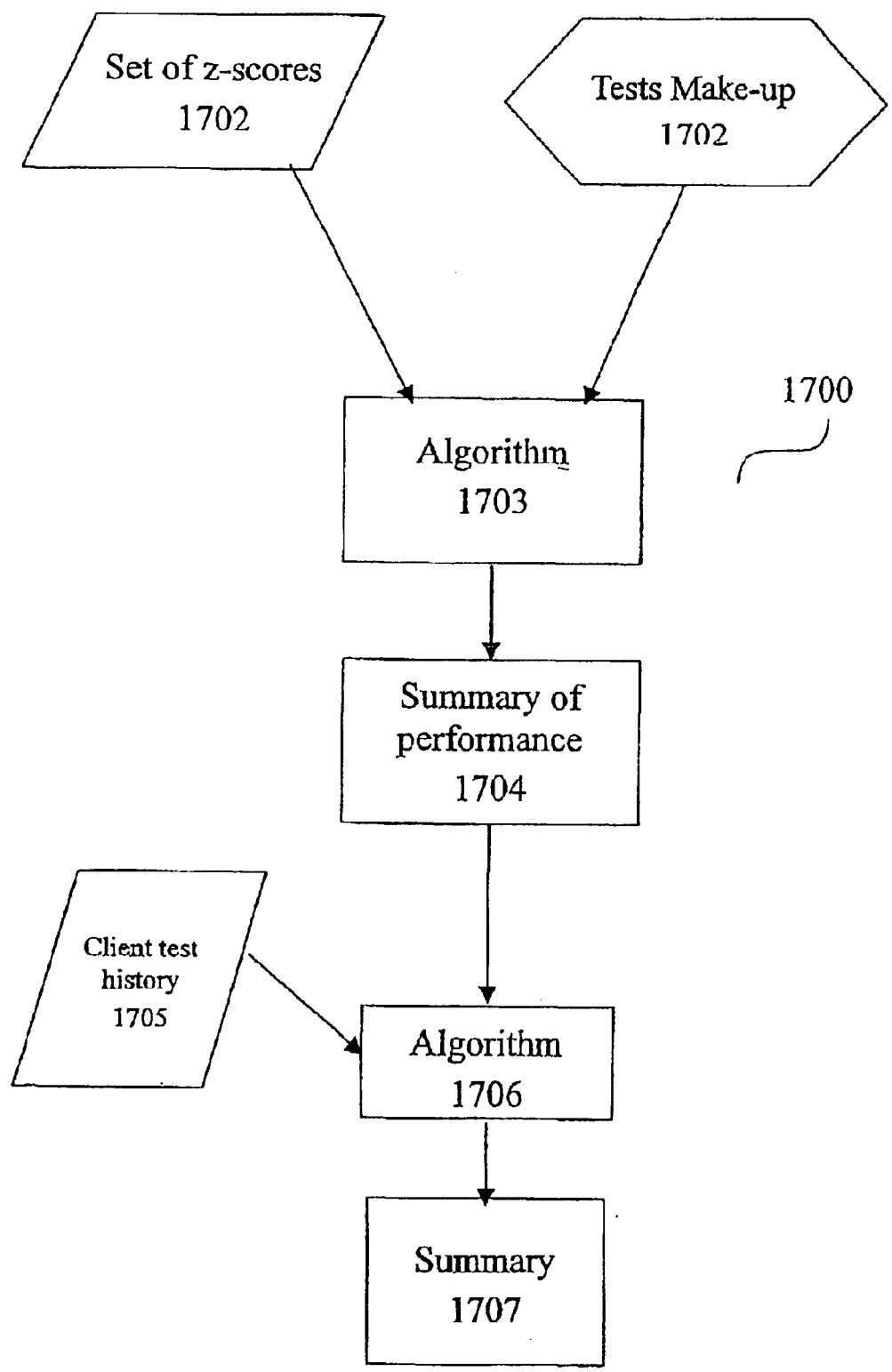
FIG. 17 illustrates a schematic view characterizing the steps of the interpretation of a test battery carried out in accordance with the software driven protocol for managing a virtual clinical neuro-psychological testing program.

Referring to the stage of interpretation of test battery (1208), this is further enlarged upon in FIG. 17, which illustrates a schematic view characterizing the steps of the interpretation of a test battery (1700) carried out in accordance with the software driven protocol for managing a virtual clinical neuro psychological testing program. This interpretation emanates from a set of z-scores (1701) for an entire battery and information (1702) on the make of the tests in the battery in terms of the brain function tested. These are applied to an algorithm step (1703), for comparing statistical results from multiple tests that overlap regarding the brain functions tested. The level of difficulty and extent of assessment differs between tests, and then lead to a summary of performance (1704) in terms of brain functions tested (for each function, whether normal or abnormal, and extent of abnormality). Thereafter, based on the client testing history (1705) from the database, an algorithm step (1706), for incorporating past performance and to look at trends in the data, provides a summary of brain functions tested (1707), as change over time is personalized for the client.

Technology relating to presentation of test battery and data acquisition:

1. Visual and auditory presentation of instructions for each test.
2. Computerized visual and auditory stimuli.
3. Computerized questionnaire for the clinician.
4. Computerized questionnaire for the client, parent, or caregiver.
5. Animation of testing scenario, similar to computer games.
6. Client interacts with the testing program via standard or customized computer input devices, including but not limited to keyboard, mouse, joystick, digitizing tablet, touch-pad, "games" controller, customized keyboard, microphone, touch-screen.
7. Client normal activity responses including all types of communication devices.
8. Testing software records all data in the form of stimuli and responses.

Depending on the nature of the test, responses may be in the form of binary data, ordinal data, discrete data (scalar values such as reaction time and movement time), or continuous digitized data (a vector or matrix of data that may represent performance such as movement trajectory, sequence or key presses, or vocal response inputs), or on-line or off-line derived parameters (data extracted from the raw data summarizing the key features of the response, such as response accuracy, total movement time, negative response bias index, etc.)

Technology relating to analysis and interpretation of test results:

1. 'Raw' data are analyzed to produce output parameters according to the design of the test and the nature of the data thereof. This step summarizes the data set from each test into a set of relevant numbers.
2. For binary or ordinal data collected via questionnaires or rating scales, the data analysis consists of weighted combinations of individual responses for each subsection of the test. These are then compared to relevant normative data, resulting in a statistically relevant score (e.g. z-score) for each mental or motor function assessed by the test.
3. In the case of continuous digitized data collected from mouse, joystick, or other input device, data are analyzed by different time and frequency domain mathematical techniques to extract output performance parameters relevant to the test. These generally include, but are not limited to, accuracy, reaction time, movement time, tremor amplitude and frequency, indices of learning.
4. Performance parameters thus computed are compared to relevant normative data using statistical methods to determine whether individual output parameters are statistically different from reference data, based on predetermined criteria for significance (e.g. z-score). These are referred to as test results.
5. Test results from some or all tests in the testing battery are compared for patterns of convergence or divergence from expected trends. As each test assesses a fixed set of mental or motor functions, and as test batteries are constructed to provide overlap or redundancy between different tests in the battery, there are predicted patterns of convergence of test results that are known to (or intended to) test the same or similar mental or motor functions. This may utilize statistical methodologies, automata, rule-based, neural network, or other methods.
6. Testing battery interpretation is a summary of the mental or motor functions tested in the battery; for each an indication of normality or abnormality as compared to relevant reference populations, the confidence at which the interpretation was reached based on consistencies or inconsistencies in the test results, and in certain cases the degree of abnormality.
7. Client-specific interpretation is arrived at by comparing test interpretation to the client's testing history.
8. Recommendations for further testing or for referral to other health care evaluation are provided, based on the interpretation. This may be derived from an expert system utilizing other demographic or other information provided by the clinician, client, or caretaker, in combination with the test battery interpretation.

Construction of Test Batteries

Test batteries are constructed to focus on specific diagnostic or therapeutic issues. Different options are available according to the preference of the user.

1. Function-related batteries are constructed to comprehensively test one or more brain functions. This may be appropriate for research use or for when there is a focused clinical question requiring thorough testing of only one or a few areas of brain function.

Technology: Done using a look-up table of attributes of available tests.

2. Symptom-related batteries are constructed to characterize specific symptoms or complaints, as relevant to diagnosis and clinical follow-up. These are designed to test brain functions that are directly or tangentially related to the symptom, as well as brain functions that may aid in including or excluding certain disease entities from the differential diagnosis.

Technology: Done using an expert system containing known neuro-psychological deficits from experimental and clinical literature.

3. Disease-related batteries are constructed for use when following a client with a known disease entity. Here, the batteries are designed to test brain functions that are known to be (or suspected to be) affected by the disease or its treatment. These may provide useful data to the clinician to determine the stage of the disease, provide prognostic data, and guide treatment decisions. These are considered essential for evaluating new or experimental therapies for specific disease entities or syndromes.

Technology: Done using an expert system containing known neuro-psychological deficits from experimental and clinical literature.

4. Custom batteries are constructed according to specific questions posed by the clinician, or suggested by a rule-based system of the present invention, which evaluates the client testing history.

Technology: Done using an expert system containing known neuro-psychological deficits from experimental and clinical literature.

5. Cognitive-Rehabilitation testing batteries are constructed for situations where the client is a participant in a cognitive or motor rehabilitation program utilizing computerized tests (described below). Here, the testing batteries are chosen automatically by the 'computer' to be independent of the interactive computer exercises used for the individualized cognitive rehabilitation program. The test batteries are chosen to assess progress on the cognitive rehabilitation program, based on both the client's previous testing history and treatment plan and progress. Therefore, each battery is designed to focus on specific brain functions, as applicable to the individual client. This type of testing provides useful data to the rehabilitation professionals (psychiatrist, occupational therapist, physical therapist, speech therapist, cognitive therapist, others) caring for the client.

Technology: Done using an expert system containing known neuro-psychological deficits from experimental and clinical literature.

6. Self-improvement batteries are constructed similar to the function-related batteries, except to provide for the purpose of the client to practice on certain cognitive or motor skills. Here, the tests will consist of those with sufficiently steep learning curves, randomize-able parameters, and multiple levels of difficulty.

Choice of Test Batteries

The clinician may choose appropriate test batteries with the help of an embodiment of a rule base system of the present invention:

1. Choose from a list of standard batteries. A list of batteries can be accessed according to an index, categorized by type of use. Subcategories include symptom and disease-related batteries, each containing a description of the test including length of test, brain functions tested, intended use, level of difficulty.

2. Test battery 'wizard' to guide clinician in choice of battery, with recommendation based on client testing history. This consists of a decision-tree algorithm that poses questions to the user, and proceeds according to choice of an answer from a menu. At each step, the user verifies the choice.

a) Alternatively, a free data entry field is available for the user to enter his answer. An algorithm will search from a list of keyword for the best fit (like Mesh headings from Grateful Med).

b) Eventually, the algorithm suggests the appropriate test battery that best satisfies the criteria requested by the user.

c) If the user's criteria are not satisfied by the available batteries, or if the user refuses the batteries suggested by the wizard, then an option is given for formation of a custom battery. The wizard may suggest the need for formation of a custom test battery.

3. Formation of custom test battery:

a) According to criteria posed by the user in the 'wizard'.

b) According to results of client's previous testing history.

Algorithm for hierarchical testing (within each testing battery chosen as above)

Once an appropriate battery is selected, a short screening battery is presented. Based on the results of the screening battery, the following paths might be automatically chosen:

1. If the client is unable to perform the tests because of insufficient level of arousal, attention capacity, or language skills, then the testing is terminated.

2. If the results indicate high level of performance, then a detailed high-level testing battery is presented.

3. If the results indicate low level of performance, then a detailed low-level testing battery is presented.

4. Note: for any given test battery the difference between the high-level and low-level options may be different tests (as some tests are geared either for high or low ability), or the same test set for different levels of difficulty.

5. Each testing battery focuses on a small set of brain functions, but screens additional brain functions. The interpretation for the battery includes recommendation for further in-depth testing of those screened brain functions that were found abnormal.

Management of Test Batteries

1. Test batteries are stored in a database. The database is referenced by multiple fields, including but not limited to: name of test, category of test, symptoms, diseases, intended uses, brain functions tested.

2. As custom batteries are built, they are added to the test battery database.

Technology relating to dynamic development of normative values based on large body of data:

1. Data from each test is added to the database for that test, stored with user-input clinical data; including age, level of difficulty, clinical condition (based on client input; e.g. normal, known disease, suspected disease), special circumstances (e.g. Parkinsonian ON/OFF state, time of day), etc.

Technology: as established for developing norms for psychological tests;

Special attention to method for adjusting for
a) level of difficulty in the test
b) randomized factors Reliability of Clinical Data
a) Judged reliable—added to database
b) Judged unreliable—not added
   Technology: methods for checking internal consistency and sufficient user input 2. For scoring (interpretation) of tests: appropriate reference norms are compiled from database, and z-score is computed.
   Technology: application of statistical models, such as linear, multiple, or logistic data regression may be appropriate.

Test parameter randomization—enhancing validity of repeated testing

For certain tests, whenever possible and appropriate, some non-essential test parameters are varied in a pseudo-random fashion:

1. Essential parameters are defined as those that directly relate to the brain functions being assessed by the test.
2. Non-essential parameters are defined as those that may be changed without affecting the brain functions being tested.

Illustration—In a test of visual acuity the essential parameter is the size of the characters on each line. A non-essential parameter is the actual sequence of characters on each line. It is either assumed or known that changing the non-essential parameter will not affect the assessment of visual acuity. Rather, the randomization of this parameter enhances validity of test repetition by removing practice effects or the ability of the client to memorize the sequence from trial to trial.

Technology: set of non-essential parameters determined per test design, with "expert" input. For repeat client testing, previous choices will be removed from set, and then random (or pseudo-random) choice of parameter value is applied to the present test.

What is claimed is:

1. A software driven protocol for managing a virtual clinical neuro-psychological testing program, the protocol including for each client of a plurality of clients the steps:
   a) evaluating of a prior history of the client;
   b) according to the evaluated prior history, forming an appropriate battery of tests for testing the client wherein said battery incorporates pseudo-randomization of at least one representational or organizational parameter;
   c) via a data-communications medium, interactively
      i. delivering, to the client, the formed battery of tests, and
      ii. accepting, from the client, a substantially completed response to the delivered formed battery of tests;
   d) analyzing the accepted response; and
   e) into the prior history of the client, integrating
      i. the accepted substantially completed response or
      ii. at least one analytical metric thereof.

2. The protocol according to claim 1 wherein forming an appropriate battery of tests includes choosing at least two tests for measuring at least one mental or motor function, and the tests are selected from the list of testing instruments for measuring: mental health, intelligence, IQ, memory, immediate recall, memory encoding, memory retrieval, working memory, semantic memory, procedural learning, sequence learning, conditioned response, Pavlovian learning, associative learning, implicit learning, explicit learning, block learning, motor learning, pattern matching, judgment, attention, concentration, visual-spatial perception, velocity perception, distance perception, visual searching, calculational ability, mathematical ability, abstract thinking, symbolic thinking, adaptation, sensory-motor adaptation, language, reading, naming, comprehension, classification, direction-following, vigilance, motor, sensory-motor, coordination, psychomotor performance, dexterity, motor skills, tremor, physiological tremor, simple reaction time, choice reaction time, sustained attention, selected attention, divided attention, driving safety, ballistic movement, bradykinesia, hypokinesia, akinesia, hypometria, movement speed, movement smoothness, movement accuracy, repetitive movement, accurately timed movements, bimanual coordination, hand-eye coordination, personality, scholastic performance, depression, psychosis, neurosis, anxiety, stress, post-traumatic stress, dementia, static visual acuity, dynamic visual acuity, handwriting analysis, speech analysis, voice tremor, or metrics of interacting with a testing instrument.

3. The protocol according to claim 1 wherein forming includes for at least one test in the battery of tests defining a subset of equivalent validation of testing objects and therein pseudo randomization includes randomizing amongst the substantially validated testing objects.

4. The protocol according to claim 1 wherein evaluating includes a disclosure of information by the client.

5. The protocol according to claim 1 wherein evaluating of a prior history of the client includes: interactively merging practitioner recommendations for this client into the prior history.

6. The protocol according to claim 1 further including the step of scheduling a next evaluating of a prior history of the client.

7. The protocol according to claim 1 wherein analyzing the accepted response includes: calculating an analytical metric of client performance using the accepted response in the formed battery of tests of at least one client performance parameter from the accepted response of a test in the formed battery of tests.

8. The protocol according to claim 1 wherein analyzing the accepted response includes: calculating an analytical metric of client performance using the accepted response in the formed battery of tests of at least one convergence parameter from the accepted response of at least two tests in the formed battery of tests.

9. The protocol according to claim 1 wherein analyzing the accepted response includes for a client: applying a rule-based criteria for quantifying at least one difference between a pair of metrics selected from the list:
   a) the evaluated prior history of the client;
   b) a metric of expected performance on at least one test of the formed battery of tests;
   c) actual performance on at least one test of the formed battery of tests; and
   d) normative values based on large body of data for at least one test of the formed battery of tests.

10. The protocol according to claim 1 wherein a test of the delivered and accepted formed battery of tests includes a metric of the clients interaction with a client's peripheral device, and the device is selected from the list: Color graphic display; B/W graphic display; Audio speaker; Audio stereophonic headphones; Mouse; Joystick; Roller-ball; Keyboard; Galvanic skin response monitor; Web-cam camera; Microphone; personal communication device, Touch pad; or Touch screen.

11. A clinical protocol for normal-use activities, the protocol including the steps of:
  a) for substantially each client in an ensemble of clients, monitoring at least one metric of normal-use activities;
  b) for substantially each metric of the at least one metric of normal use activities, until a predetermined threshold of validation is achieved for an ensemble of clients, first managing a virtual clinical neuro-psychological testing program for substantially each client in the ensemble; and correlating analytical metrics derived from the neuro-psychological testing program with the monitored metrics of normal-use activities, thereby validating at least one of the monitored metrics of normal-use activities as a neuro-psychological metric; and
  c) for substantially each validated metric of the at least one metric of normal use activities, second managing a virtual clinical neuro-psychological testing program for at least one client wherein a validated normal-use activity metric is used as a classical testing instrument.

12. The clinical protocol according to claim 11 wherein for substantially each client in an ensemble of clients, monitoring at least one metric of normal-use activities includes downloading a plug-in to the client's machine, installing the plug-in, or uploading data collected by the plug-in.

13. The clinical protocol according to claim 11 wherein a metric of normal use activity of the monitored at least one metric of normal use activities is calculated by measuring an activity selected from the list of copying, printing, pasting, editing, inserting, formatting, exchanging tasks, web surfing, backspacing, deleting or shifting.

14. The clinical protocol according to claim 11 wherein for substantially each client in an ensemble of clients, monitoring at least one metric of normal-use activities includes, copying, pasting, editing, inserting, formatting, exchanging tasks, web surfing, backspacing, deleting or shifting.

15. The clinical protocol according to claim 11 wherein for substantially each client in an ensemble of clients, monitoring at least one metric of normal-use activities includes computer related interactivity, wireless activity, voice prints frequency analysis, mouse tremor, Geographic Positioning System tremor, key strokes, or special case use.

16. The clinical protocol according to claim 11 wherein that first managing and second managing include the steps:
  a) evaluating a prior history of the client;
  b) according to the evaluated prior history, forming an appropriate battery of tests wherein said battery incorporates pseudo-randomization of at least one representational or organizational parameter;
  c) via a data communications system, interactively
    i. delivering, to the client, the formed battery of tests, and
    ii. accepting, from the client, a substantially completed response to the delivered formed battery of tests;
  d) analyzing the accepted response; and
  e) into the prior testing history of the client, integrating
    i. the accepted substantially completed response or
    ii. at least one analytical metric thereof.

17. The protocol according to claim 16 wherein forming an appropriate battery of tests includes choosing at least two tests for measuring at least one mental or motor function, and the tests are selected from the list of testing instruments for measuring: mental health, intelligence, IQ, memory, immediate recall, memory encoding, memory retrieval, working memory, semantic memory, procedural learning, sequence learning, conditioned response, Pavlovian learning, associative learning, implicit learning, explicit learning, block learning, motor learning, pattern matching, judgment, attention, concentration, visual-spatial perception, velocity perception, distance perception, visual searching, calculational ability, mathematical ability, abstract thinking, symbolic thinking, adaptation, sensory-motor adaptation, language, reading, naming, comprehension, classification, direction-following, vigilance, motor, sensory-motor, coordination, psychomotor performance, dexterity, motor skills, tremor, physiological tremor, simple reaction time, choice reaction time, sustained attention, selected attention, divided attention, driving safety, ballistic movement, bradykinesia, hypokinesia, akinesia, hypometria, movement speed, movement smoothness, movement accuracy, repetitive movement, accurately timed movements, bimanual coordination, hand-eye coordination, personality, scholastic performance, depression, psychosis, neurosis, anxiety, stress, post-traumatic stress, dementia, static visual acuity, dynamic visual acuity, handwriting analysis, speech analysis, voice tremor, or metrics of interacting with a testing instrument.

18. The protocol according to claim 16 wherein forming includes for at least one test in the battery of tests defining a subset of equivalent validation of testing objects and therein pseudo randomization includes randomizing amongst the substantially validated testing objects.

19. The protocol according to claim 16 wherein evaluating includes a disclosure of information by the client.

20. The protocol according to claim 16 wherein evaluating of a prior history of the client includes: interactively merging practitioner recommendations for this client into the prior history.

21. The protocol according to claim 16 further including the step of scheduling a next evaluating of a prior history of the client.

22. The protocol according to claim 16 wherein analyzing the accepted response includes: calculating an analytical metric of client's performance using the accepted response in the formed battery of tests of at least one client performance parameter from the accepted response of a test in the formed battery of tests.

23. The protocol according to claim 16 wherein analyzing the accepted response includes: calculating an analytical metric of client's performance using the accepted response in the formed battery of tests of at least one convergence parameter from the accepted response of at least two tests in the formed battery of tests.

24. The protocol according to claim 16 wherein analyzing the accepted response includes for a client: applying a rule-based criteria for quantifying at least one difference between a pair of metrics selected from the list:
  a) the evaluated prior history of the client;
  b) a metric of expected performance on at least one test of the formed battery of tests;
  c) actual performance on at least one test of the formed battery of tests; and
  d) normative values based on large body of data for at least one test of the formed battery of tests.

25. The protocol according to claim 16 wherein a test of the delivered and accepted formed battery of tests includes a metric of the clients interaction with a client's peripheral device, and the device is selected from the list: Color graphic display; B/W graphic display; Audio speaker; Audio stereophonic headphones; Mouse; Joystick; Roller-ball; Keyboard; Galvanic skin response monitor; Web-cam camera; Microphone; personal communication device, Touch pad; or Touch screen.

26. The clinical protocol according to claim 11 wherein first managing and second managing include the steps:
   a) evaluating a prior history of the client;
   b) according to the evaluated prior history, forming an appropriate battery of tests for testing the client wherein said battery incorporates pseudo-randomization of at least one representational or organizational parameter;
   c) via a data-communications medium, interactively
      i. delivering, to the client, the formed battery of tests, and
      ii. accepting, from the client, a substantially completed response to the delivered formed battery of tests;
   d) analyzing the accepted response; and
   e) into the prior history of the client, integrating
      i. the accepted substantially completed response or
      ii. at least one analytical metric thereof.

27. A software driven protocol for managing a virtual clinical neuro-psychological dynamic hierarchical testing program, the protocol including for each client of a plurality of clients the steps:
   a) evaluating of a prior history of the client;
   b) according to the evaluated prior history,
      i. interactively forming an appropriate battery of tests for testing the client wherein said battery incorporates pseudo-randomization of at least one representational or organizational parameter,
      ii. via a data-communications medium, interactively delivering, to the client, the formed battery of tests,
      iii. accepting, from the client, a substantially completed response to the delivered formed battery of tests,
      iv. analyzing the accepted response, and
      v. returning to step b)i until complete; and
   c) into the prior history of the client, integrating
      i. the accepted substantially completed response or
      ii. at least one analytical metric thereof.

28. The protocol according to claim 27 wherein forming an appropriate battery of tests includes choosing at least two tests for measuring at least one mental or motor function, and the tests are selected from the list of testing instruments for measuring: mental health, intelligence, IQ, memory, immediate recall, memory encoding, memory retrieval, working memory, semantic memory, procedural learning, sequence learning, conditioned response, Pavlovian learning, associative learning, implicit learning, explicit learning, block learning, motor learning, pattern matching, judgment, attention, concentration, visual-spatial perception, velocity perception, distance perception, visual searching, calculational ability, mathematical ability, abstract thinking, symbolic thinking, adaptation, sensory-motor adaptation, language, reading, naming, comprehension, classification, direction-following, vigilance, motor, sensory-motor, coordination, psychomotor performance, dexterity, motor skills, tremor, physiological tremor, simple reaction time, choice reaction time, sustained attention, selected attention, divided attention, driving safety, ballistic movement, bradykinesia, hypokinesia, akinesia, hypometria, movement speed, movement smoothness, movement accuracy, repetitive movement, accurately timed movements, bimanual coordination, hand-eye coordination, personality, scholastic performance, depression, psychosis, neurosis, anxiety, stress, post-traumatic stress, dementia, static visual acuity, dynamic visual acuity, handwriting analysis, speech analysis, voice tremor, or metrics of interacting with a testing instrument.

29. The protocol according to claim 27 wherein forming includes for at least one test in the battery of tests defining a subset of equivalent validation of testing objects and therein pseudo randomization includes randomizing amongst the substantially validated testing objects.

30. The protocol according to claim 27 wherein evaluating includes a disclosure of information by the client.

31. The protocol according to claim 27 wherein evaluating of a prior history of the client includes: interactively merging practitioner recommendations for this client into the prior history.

32. The protocol according to claim 27 further including the step of scheduling a next evaluating of a prior history of the client.

33. The protocol according to claim 27 wherein analyzing the accepted response includes: calculating an analytical metric of client performance using the accepted response in the formed battery of tests of at least one client performance parameter from the accepted response of a test in the formed battery of tests.

34. The protocol according to claim 27 wherein analyzing the accepted response includes: calculating an analytical metric of client performance using the accepted response in the formed battery of tests of at least one of at least one convergence parameter from the accepted response of at least two tests in the formed battery of tests.

35. The protocol according to claim 27 wherein analyzing the accepted response includes for a client, applying a rule-based criteria for quantifying at least one difference between a pair of metrics selected from the list:
   a) the evaluated prior history of the client;
   b) a metric of expected performance on at least one test of the formed battery of tests;
   c) actual performance on at least one test of the formed battery of tests; and
   d) normative values based on large body of data for at least one test of the formed battery of tests.

36. The protocol according to claim 27 wherein a test of the delivered and accepted formed battery of tests includes a metric of the clients interaction with a client's peripheral device, and the device is selected from the list: Color graphic display; B/W graphic display; Audio speaker; Audio stereophonic headphones; Mouse; Joystick; Roller-ball; Keyboard; Galvanic skin response monitor; Web-cam camera; Microphone; personal communications device, Touch pad; or Touch screen.

37. The protocol according to claim 27 further includes the steps of:
   a) establishing, upgrading and maintaining as appropriate, a validity metric for a substantially non-validated test, for each client of an ensemble of clients;
   b) introducing a substantially non-validated test into the formed battery of tests;
   c) analyzing responses to the substantially non-validated tests; and
   d) correlating responses with the responses from the other tests in the formed battery of tests.

38. The clinical protocol according to claim 37, wherein establishing, upgrading and maintaining include:
   a) for substantially each client in an ensemble of clients, monitoring at least one metric of normal-use activities;
   b) for substantially each metric of the at least one metric of normal-use activities, until a predetermined threshold of validation is achieved for an ensemble of clients, first managing a virtual clinical neuro-psychological testing program for substantially each client in the ensemble; and correlating analytical metrics derived from the neuro-psychological testing program with the monitored metrics of normal-use activities, thereby validating at least one of the monitored metrics of normal-use activities as a neuro-psychological metric; and c) for substantially each validated metric of the at least one metric of normal-use activities, second managing a virtual clinical neuro-psychological testing program for at least one client wherein a validated normal-use activity metric is used as a classical testing instrument.

39. The clinical protocol according to claim 38 wherein for substantially each client in an ensemble of clients, monitoring at least one metric of normal-use activities includes downloading a plug-in to the client's machine, installing plug-ins, uploading data collected by the plug-in.

40. The clinical protocol according to claim 38 wherein a metric of normal use activity of the monitored at least one metric of normal use activities is calculated by measuring an activity selected from the list of copying, printing, pasting, editing, inserting, formatting, exchanging tasks, web surfing, backspacing, deleting and shifting.

41. The clinical protocol according to claim 38 wherein for substantially each client in an ensemble of clients, monitoring at least one metric of normal-use activities includes copying, pasting, editing, inserting, formatting, backspacing, deleting, shifting and web surfing.

42. The clinical protocol according to claim 38 wherein for substantially each client in an ensemble of clients, monitoring at least one metric of normal-use activities includes computer related interactivity, wireless activity, voice prints frequency analysis, mouse tremor, Geographic Positioning System tremor, key strokes, and special case use.

43. The clinical protocol according to claim 38 wherein that first managing and second managing include the steps:
  a) evaluating a prior history of the client;
  b) according to the evaluated prior history, forming an appropriate battery of tests for testing the client wherein said battery incorporates pseudo-randomization of at least one representational or organizational parameter;
  c) via a data-communications medium, interactively
    i. delivering, to the client, the formed battery of tests, and
    ii. accepting, from the client, a substantially completed response to the delivered formed battery of tests;
  d) analyzing the accepted response; and
  e) into the prior history of the client, integrating
    i. the accepted substantially completed response or
    ii. at least one analytical metric thereof.

44. A software driven protocol for managing a virtual clinical neuro-psychological testing program based on normal use activities, the protocol including for each client of a plurality of clients the steps:
  a) evaluating of a prior history of the client;
  b) according to the evaluated prior history, forming at least one normal use activity factor of tests for testing the client wherein said at least one normal use activity factor incorporates pseudo-randomization of at least one representational or organizational parameter;
  c) via a data-communications medium, interactively
    i. delivering the formed at least one normal use activity factor tests to the client,
    ii. the client substantially completing the normal use activity factor tests, and
    iii. accepting, from the client, a substantially completed response to the delivered normal use activity factor tests;
  d) analyzing the accepted response; and
  e) into the prior history of the client, integrating
    i. the accepted substantially completed response or
    ii. at least one analytical metric thereof.

45. The protocol according to claim 44 wherein forming an appropriate battery of tests includes choosing at least two tests for measuring at least one mental or motor function, and the tests are selected from the list of testing instruments for measuring: mental health, intelligence, IQ, memory, immediate recall, memory encoding, memory retrieval, working memory, semantic memory, procedural learning, sequence learning, conditioned response, Pavlovian learning, associative learning, implicit learning, explicit learning, block learning, motor learning, pattern matching, judgment, attention, concentration, visual-spatial perception, velocity perception, distance perception, visual searching, calculational ability, mathematical ability, abstract thinking, symbolic thinking, adaptation, sensory-motor adaptation, language, reading, naming, comprehension, classification, direction-following, vigilance, motor, sensory-motor, coordination, psychomotor performance, dexterity, motor skills, tremor, physiological tremor, simple reaction time, choice reaction time, sustained attention, selected attention, divided attention, driving safety, ballistic movement, bradykinesia, hypokinesia, akinesia, hypometria, movement speed, movement smoothness, movement accuracy, repetitive movement, accurately timed movements, bimanual coordination, hand-eye coordination, personality, scholastic performance, depression, dynamic visual acuity, handwriting analysis, speech analysis, voice tremor, or metrics of interacting with a testing instrument.

46. The protocol according to claim 44 wherein forming includes for at least one test in the battery of tests defining a subset of equivalent validation of testing objects and therein pseudo randomization includes randomizing amongst the substantially validated testing objects.

47. The protocol according to claim 44 wherein evaluating includes a disclosure of information by the client.

48. The protocol according to claim 44 wherein evaluating of a prior history of the client, includes interactively merging practitioner recommendations for this client into the prior history.

49. The protocol according to claim 44 further including the step of scheduling a next evaluating of a prior history of the client.

50. The protocol according to claim 44 wherein analyzing the accepted response includes: calculating an analytical metric of client performance using the accepted response in the formed battery of tests of at least one client performance parameter from the accepted response of a test in the formed battery of tests.

51. The protocol according to claim 44 wherein analyzing the accepted response includes: calculating an analytical metric of client performance using the accepted response in the formed battery of tests of at least one convergence parameter from the accepted response of at least two tests in the formed battery of tests.

52. The protocol according to claim 44 wherein analyzing the accepted response includes: applying a rule-based criteria for quantifying at least one difference between a pair of metrics selected from the list:
  a) the evaluated prior history of the client;
  b) the client's expected performance on at least one test of the formed battery of tests;
  c) the clients actual performance on at least one test of the formed battery of tests; and d) normative values based on large body of data for at least one test of the formed battery of tests.

53. The protocol according to claim 44 wherein a test of the delivered and accepted formed battery of tests includes a metric of the clients interaction with a client's peripheral device, and the device is selected from the list: Color graphic display; B/W graphic display; Audio speaker; Audio stereophonic headphones; Mouse; Joystick; Roller-ball; Keyboard; Galvanic skin response monitor; Web-cam camera; Microphone; personal communication device; Touch pad; or Touch screen.

54. The clinical protocol according to claim 44 wherein for substantially each client in an ensemble of clients, monitoring at least one metric of normal-use activities includes downloading a plug-in to the client's machine, installing plug-ins or uploading data collected by the plug-in.

55. The clinical protocol according to claim 44 wherein for substantially each client in an ensemble of clients, monitoring at least one metric of normal-use activities includes copying, pasting, editing, inserting, formatting, backspacing, deleting, shifting or web surfing.

56. The clinical protocol according to claim 44 wherein for substantially each client in an ensemble of clients, monitoring at least one metric of normal-use activities includes computer related interactivity, wireless activity, voice prints frequency analysis, mouse tremor, Geographic Positioning System tremor, key strokes, or special case use.

57. The protocol according to claim 27 further includes the steps of:

a) establishing, upgrading and maintaining as appropriate, a validity metric for a substantially non-validated test, for each client of an ensemble of clients;

b) introducing a substantially non-validated test into the formed battery of tests;

c) analyzing responses to the substantially non-validated tests; and d) correlating responses with the responses from the other tests in the formed battery of tests.

* * * * *